US012778694B2

(12) United States Patent
Takahashi et al.

(10) Patent No.: US 12,778,694 B2
(45) Date of Patent: Nov. 3, 2026

(54) SURGICAL INSTRUMENT

(71) Applicant: MEDICAROID CORPORATION, Kobe (JP)

(72) Inventors: Kaoru Takahashi, Kobe (JP); Gen Kurihara, Tokyo (JP)

(73) Assignee: MEDICARDIO CORPORATION, Kobe (JP)

( * ) Notice: Subject to any disclaimer, the term of this patent is extended or adjusted under 35 U.S.C. 154(b) by 182 days.

(21) Appl. No.: 18/791,468

(22) Filed: Aug. 1, 2024

(65) Prior Publication Data

US 2025/0049524 A1 Feb. 13, 2025

(30) Foreign Application Priority Data

Aug. 8, 2023 (JP) ................................ 2023-129598
Aug. 8, 2023 (JP) ................................ 2023-129608

(51) Int. Cl.

*A61B 34/30* (2016.01)
*A61B 18/14* (2006.01)
*A61B 34/35* (2016.01)
*A61B 18/00* (2006.01)

(52) U.S. Cl.

CPC .......... *A61B 34/35* (2016.02); *A61B 18/1445* (2013.01); *A61B 2018/00208* (2013.01); *A61B 2018/00589* (2013.01); *A61B 2034/301* (2016.02); *A61B 2034/305* (2016.02)

(58) Field of Classification Search

CPC ...... A61B 18/1445; A61B 2018/00208; A61B 2018/00589; A61B 34/35; A61B 34/71; A61B 2034/301; A61B 2034/305
See application file for complete search history.

(56) References Cited

U.S. PATENT DOCUMENTS

| | | | |
|---|---|---|---|
| 6,994,708 B2 | 2/2006 | Manzo |
| 7,306,597 B2 | 12/2007 | Manzo |
| 10,420,620 B2 | 9/2019 | Rockrohr |
| 10,639,805 B2 | 5/2020 | Saraliev et al. |
| 10,743,955 B2 | 8/2020 | Rockrohr |
| 10,758,298 B2 | 9/2020 | Felder et al. |
| 10,779,897 B2 | 9/2020 | Rockrohr |

(Continued)

FOREIGN PATENT DOCUMENTS

| | | |
|---|---|---|
| JP | 6961733 B2 | 11/2021 |
| WO | 2019/136041 A1 | 7/2019 |

*Primary Examiner* — Khadijeh A Vahdat
(74) *Attorney, Agent, or Firm* — METROLEX IP LAW GROUP, PLLC; Robert L. Scott, Esq.

(57) ABSTRACT

A surgical instrument may include: a wrist joint connected to a shaft and including first and second joints; an end effector connected to the wrist joint; an elongate element connected to the end effector; at least four drive shafts; and a lever configured to move the elongate element. The at least four drive shafts comprise a first drive shaft configured to roll the shaft, second and third drive shafts configured to pitch the first joint and yaw the second joint, and a fourth drive shaft configured to move the elongate element, and the lever includes an arm, an engagement portion provided to one side of the arm and engaged with the elongate element, and a shaft portion that is provided to the other side of the arm and is rotatably arranged on the base so as to move the engagement portion by a driving force from the fourth drive shaft.

20 Claims, 15 Drawing Sheets

(56) References Cited

U.S. PATENT DOCUMENTS

| | | | |
|---|---|---|---|
| 11,065,072 | B2 | 7/2021 | Rockrohr |
| 11,518,048 | B2 | 12/2022 | Saraliev et al. |
| 11,666,395 | B2 | 6/2023 | Rockrohr |
| 2014/0338477 | A1 | 11/2014 | Donlon et al. |
| 2015/0202013 | A1 | 7/2015 | Teichtmann et al. |
| 2017/0252096 | A1 | 9/2017 | Felder et al. |
| 2019/0192241 | A1 | 6/2019 | Xu et al. |
| 2019/0201137 | A1* | 7/2019 | Shelton, IV ........... G16H 50/20 |
| 2020/0197112 | A1* | 6/2020 | Chin .................. A61B 18/1445 |
| 2020/0237453 | A1 | 7/2020 | Anglese |
| 2021/0059777 | A1 | 3/2021 | Overmyer et al. |
| 2021/0153927 | A1 | 5/2021 | Ross et al. |
| 2021/0177495 | A1 | 6/2021 | Ross et al. |
| 2021/0307853 | A1 | 10/2021 | Rockrohr |
| 2021/0322116 | A1 | 10/2021 | Swayze et al. |
| 2023/0000578 | A1 | 1/2023 | Moubarak |

* cited by examiner

SURGICAL INSTRUMENT

CROSS REFERENCE TO RELATED APPLICATIONS

This application claims priority based on 35 USC 119 from prior Japanese Patent Applications No. 2023-129598 filed on Aug. 8, 2023, entitled "SURGICAL INSTRUMENT" and No. 2023-129608 filed on Aug. 8, 2023, entitled "SURGICAL INSTRUMENT", the entire contents of all of which are incorporated herein by reference.

BACKGROUND

The disclosure may relate to a surgical instrument.

In a related art, there has been a surgical instrument including drive shafts (for example, Patent Document 1: U.S. Pat. No. 7,306,597)

Patent Document 1 discloses a surgical instrument includes a drive shaft, a disk fixed to the drive shaft, an eccentric cam pin provided to the disk, a drive bar that is engaged with the eccentric cam pin, a pivot drive shaft that serves as a pivot axis of the drive bar, a core rod that moves back and forth in a longitudinal direction of an elongate shaft as the drive bar rotates about the pivot drive shaft, and blades of an end effector that opens and closes as the core rod moves back and forth. The surgical instrument disclosed in Patent Document 1 discloses four drive shafts extending vertically from a base, and among the four drive shafts, two drive shafts are used to move the core rod back and forth to drive the end effector, one drive shaft is used to rotate the elongate shaft.

Patent Document 1: U.S. Pat. No. 7,306,597

SUMMARY

However, in Patent Document 1, the two drive shafts are used to move the core rod back and forth to drive the end effector, so there is an insufficient number of drive shafts to perform pitch and yaw joint movements of the end effector, which makes it difficult to perform pitch and yaw joint movements of the end effector. Accordingly, it may be difficult to roll the shaft, pitch and yaw the end effector, and move the rod (elongate element) to operate the end effector in the longitudinal direction of the shaft, by using the four drive shafts.

An object of an embodiment of the disclosure may be to provide a surgical instrument including four drive shafts that rolls a shaft, pitches and yaws an end effector, and moves an elongate element to move the end effector in a longitudinal direction of the shaft.

An aspect of the disclosure may be a surgical instrument that may include: a housing including a base that is to be attached to a robot arm; a shaft including a proximal end connected to the base; a wrist joint connected to a distal end side of the shaft, the wrist joint including a first joint configured to perform a pitch joint movement about a first rotation axis intersecting a longitudinal direction of the shaft and a second joint configured to perform a yaw joint movement about a second rotation axis intersecting the longitudinal direction and the first rotation axis; an end effector connected to a distal end of the wrist joint; an elongate element extending in the longitudinal direction of the shaft, the elongate element including a distal end thereof connected to the end effector; at least four drive shafts provided to the base and configured to driven to rotate by driving forces from motors provided to the robot arm; and a lever configured to move the elongate element in the longitudinal direction. The at least four drive shafts comprise a first drive shaft configured to roll the shaft about an axis along the longitudinal direction of the shaft, a second drive shaft and a third drive shaft configured to pitch the first joint and yaw the second joint, and a fourth drive shaft configured to move the elongate element in the longitudinal direction of the shaft. The lever includes an arm, an engagement portion provided to one side of the arm and engaged with the elongate element, and a shaft portion that is provided to the other side of the arm and is rotatably arranged on the base so as to move the engagement portion by a driving force from the fourth drive shaft.

According to the aspect, the shaft portion of the lever, which moves the elongate element in the longitudinal direction, serves as a rotation axis of the lever, and therefore there is no need to use one of the drive shafts as the rotation axis of the lever. Accordingly, only one of the drive shafts is used to move the elongate element in the longitudinal direction of the shaft to operate the end effector. As a result, it is possible to provide the surgical instrument including the four drive shafts that can roll the shaft, pitch and yaw the end effector, and move the elongate element to move the end effector in the longitudinal direction of the shaft.

According to the aspect, it is possible to roll the shaft, pitch and yaw the end effector, and move the elongate element in the longitudinal direction of the shaft to operate to the end effector, by the four drive shafts.

DETAILED DESCRIPTION

Figure 1:
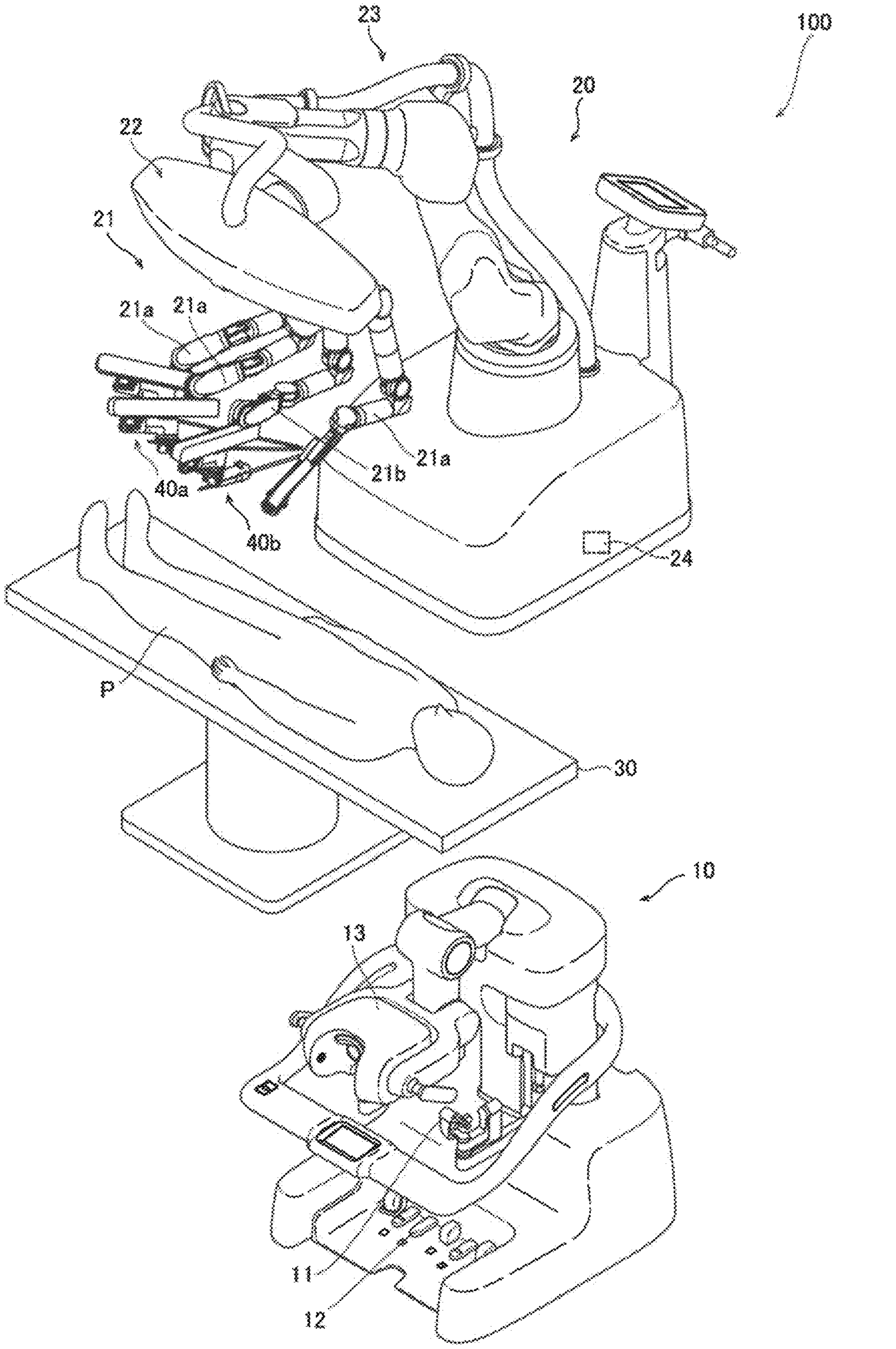
FIG. 1 is a diagram illustrating a configuration of a robotic surgical system according to an embodiment.

Descriptions are provided hereinbelow for embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Robotic Surgical System)

A configuration of a robotic surgical system 100 according to an embodiment is described with reference to FIGS. 1 and 2.

As illustrated in FIG. 1, the robotic surgical system 100 includes a remote control apparatus 10 and a patient-side apparatus 20. The remote control apparatus 10 is provided to remotely control medical equipment attached to the patient-side apparatus 20. When an operator, as a surgeon, inputs an action mode instruction to be executed by the patient-side apparatus 20, to the remote control apparatus 10, the remote control apparatus 10 transmits the action mode instruction to the patient-side apparatus 20 through a controller 24. In response to the action mode instruction transmitted from the remote control apparatus 10, the patient-side apparatus 20 operates the medical equipment, including surgical instruments 40*a* attached to robot arms 21*a* and an endoscope 40*b* attached to a robot arm 21*b*.

The patient-side apparatus 20 is positioned beside an operation table 30 on which a patient P is laid. The patient-side apparatus 20 includes plural robot arms 21*a* and 21*b*. One 21*b* of the robot arms holds the endoscope 40*b* and the other robot arms 21*a* hold the surgical instruments 40*a*. Each of the plural robot arms 21*a* and 21*b* includes plural joints. Each joint includes a driver (a driving device) including a servo-motor and a position detector such as an encoder or the like.

The arm base 22 is supported by a positioner 23 placed on the floor of an operation room. The positioner 23 includes a vertical articulated robot. The positioner 23 is configured to move the position of the arm base 22 three-dimensionally. The controller 24 is a control circuit including an arithmetic unit such as a CPU and/or the like, and a memory such as a ROM, a RAM, and/or the like.

The surgical instruments 40*a* as the medical equipment are detachably attached to distal ends of the robot arms 21*a*. The surgical instrument 40*a* includes a housing 41 (see FIG. 3), an elongate shaft 42 (see FIG. 3), and an end effector 43 (see FIG. 3). The end effector 43 may be grasping forceps, scissors, a hook, a high-frequency knife, a snare wire, a clamp, a stapler, a clip applier, an electric knife, or a needle, for example. The end effector 43 is not limited to those and can be various types of treatment tools. In surgeries using the patient-side apparatus 20, the robot arms 21*a* introduce the surgical instruments 40*a* into the body of the patient P through a cannula (trocar) placed on the body surface of the patient P.

To the distal end of the robot arm 21*b*, the endoscope 40*b* as the medical equipment is detachably attached. The endoscope 40*b* captures an image in a body cavity of the patient P. The captured image is outputted to the remote control apparatus 10. The endoscope 40*b* may be a 3D endoscope capable of capturing a three-dimensional image or a 2D endoscope. In surgeries using the patient-side apparatus 20, the robot arm 21*b* introduces the endoscope 40*b* into the body of the patient P through a trocar placed on the body surface of the patient P.

The remote control apparatus 10 is an apparatus that allows the operator to operate the medical equipment attached to the robot arms 21*a* and 21*b*. Specifically, the remote control apparatus 10 is configured to transmit action mode instructions which are inputted by the operator and are to be executed by the surgical instruments 40*a* and the endoscope 40*b*, to the patient-side apparatus 20 through the controller 24.

The action modes to be executed by the surgical instruments 40*a* include modes of actions to be taken by each surgical instrument 40*a* (a series of positions and postures) and actions to be executed by the function of each surgical instrument 40*a*. For example, in a case in which the surgical instrument 40*a* is a vessel sealer, the operational modes to be performed by the surgical instrument 40*a* include pitch and yaw rotations of the wrist of the end effector 43, opening and closing of the jaws, coagulating tissue by supplying a coagulation current to the end effector, and incising tissue by supplying a cutting current to the end effector.

The action modes to be executed by the endoscope 40*b* include the position and posture of the distal end of the endoscope 40*b* and setting of the zoom magnification, for example.

Figure 2:
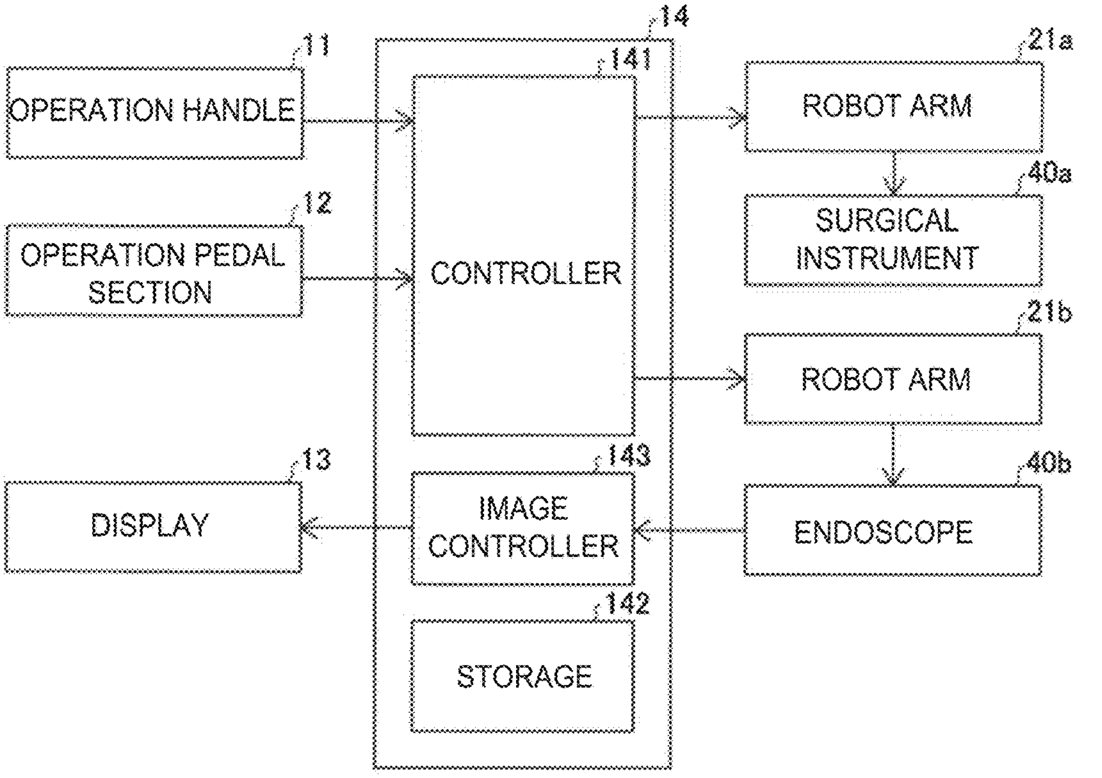
FIG. 2 is a block diagram illustrating a control-related configuration of the robotic surgical system according to an embodiment.

As illustrated in FIGS. 1 and 2, the remote control apparatus 10 includes operation handles 11, an operation pedal section 12, a display 13, and a control apparatus 14.

The operation handles 11 are provided in order to remotely operate medical equipment attached to the robot arms 21*a*. Specifically, the operation handles 11 accept operations by the operator for operating the medical equipment (the surgical instruments 40*a* and endoscope 40*b*). The operation handles 11 are composed of two operation handles 11 arranged side by side in the horizontal direction.

The operation handles 11 extend from the rear side of the remote control apparatus 10 toward the front side. The operation handles 11 are configured to move in a predetermined three-dimensional operation region.

The remote control apparatus 10 and the patient-side apparatus 20 constitute a master-slave system in terms of controlling movements of the robot arms 21*a* and 21*b*. The operation handles 11 constitute a master side operating part in the master-slave system, and the robot arms 21*a* and 21*b* to which the medical equipment is attached constitute a slave side operating part in the master-slave system. When the operator operates the operation handles 11, the movement of one of the robot arms 21*a* or 21*b* is controlled so that the distal end portion (the end effector 43 of the surgical instrument 40*a*) of the robot arm 21*a* or the distal end portion (the endoscope 40*b*) of the robot arm 21*b* moves following the movement of the operation handles 11.

The operation pedal section 12 or an operation pedal unit includes plural pedals to execute medical equipment-related functions. The plural pedals include a coagulation pedal, a cutting pedal, a camera pedal, and a clutch pedal. The plural pedals are operated by a foot of the operator.

By operating the coagulation pedal, a coagulation current is supplied to the surgical instrument 40*a* so as to coagulate the surgical site. By operating the cutting pedal, a cutting current is supplied to the surgical instrument 40*a* so as to cut the surgery site.

By operating the camera pedal, the operation handles 11 are allowed to operate the endoscope 40*b*. That is, the position and orientation of the endoscope 40*b* are controllable by the operation handles 11 while the camera pedal is being pressed. The endoscope 40*b* is controlled by using both of the right and left operation handles 11, for example.

The clutch pedal is used to temporarily disconnect operation-related connection between the operation handles 11 and the robot arms 21*a* to stop movements of the surgical instruments 40*a*. Specifically, when the clutch pedal is being pressed, the robot arms 21*a* of the patient-side apparatus 20 do not work even if the operation handles 11 are operated.

The display 13 (or a display device) is configured to display images captured by the endoscope 40*b*. The display 13 comprises a scope type display or a non-scope type display. (Note that FIG. 1 illustrates a scope type display 13.) The scope type display is a display configured in such a manner that the operator looks into the display. The non-scope type display is a display like an open-type display that includes a flat screen and the operator is able to see without looking into, such as normal displays for personal computers.

The display 13 displays a 3D image captured by the endoscope 40*b* attached to the robot arm 21*b* of the patient-side apparatus 20. Note that the display 13 may display a 2D image captured by the endoscope 40*b* provided to the patient-side apparatus 20.

As illustrated in FIG. 2, the control apparatus 14 includes a controller 141, a storage 142, and an image controller 143, for example. The controller 141 includes an arithmetic unit such as a CPU. The storage 142 includes a memory, such as a ROM and a RAM. The control apparatus 14 may be composed of a single control apparatus performing centralized control or may be composed of plural control apparatuses that perform decentralized control in cooperation with each other. The controller 141 determines whether an action mode instruction inputted by the operation handles 11 is to be executed by the robot arms 21*a* or to be executed by the endoscope 40*b*, depending on the state of the operation pedal section 12. When determining that the action mode instruction inputted by the operation handles 11 is to be executed by any one of the surgical instruments 40*a*, the controller 141 transmits the action mode instruction to the corresponding robot arm 21*a* through the controller 24. The robot arm 21*a* is thereby driven by the controller 24 and thus the movement of the surgical instrument 40*a* attached to the robot arm 21*a* is controlled.

The storage 142 stores control programs corresponding to the types of the surgical instrument 40*a*, for example. The controller 141 reads the stored control programs according to the types of the attached surgical instruments 40*a*. The action mode instructions from the operation handles 11 and/or the operation pedal section 12 of the remote control apparatus 10 thereby cause the respective surgical instruments 40*a* to perform proper movements.

The image controller 143 transmits images acquired by the endoscope 40*b* to the display 13. The image controller 143 performs processing and modifying the images when needed.

(Configurations of Surgical Instrument, Adaptor, Drape, and Robot Arm)

Figure 3:
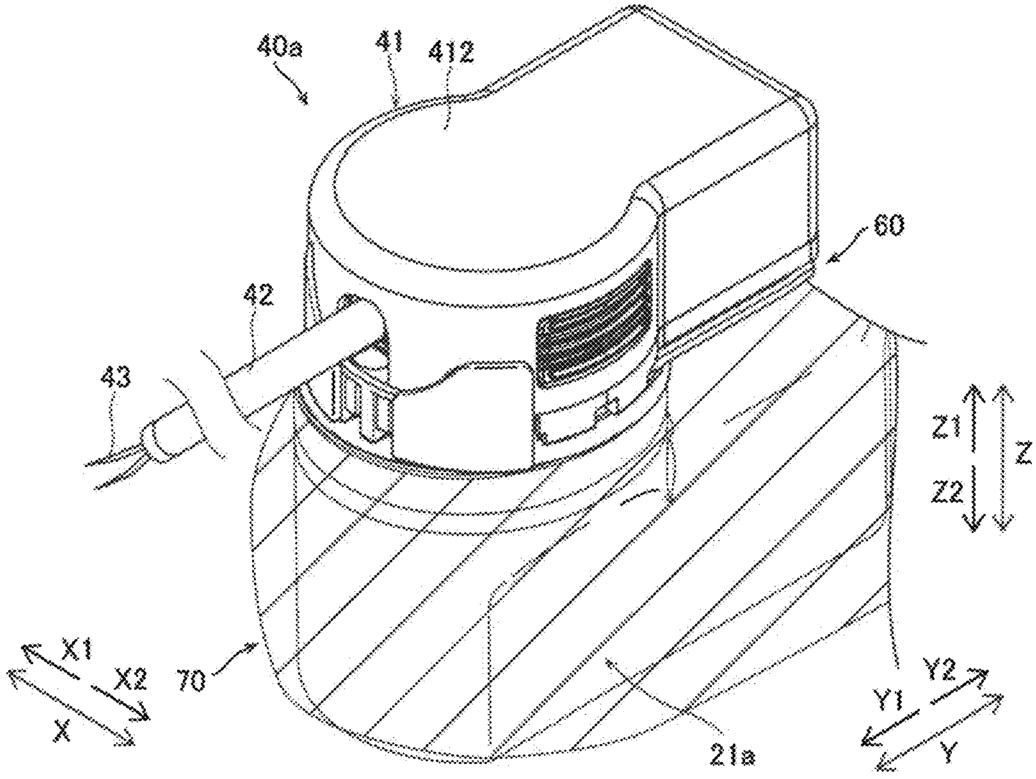
FIG. 3 is a diagram illustrating a perspective view of a state where a surgical instrument according to an embodiment is attached to a robot arm through an adaptor.
Figure 4:
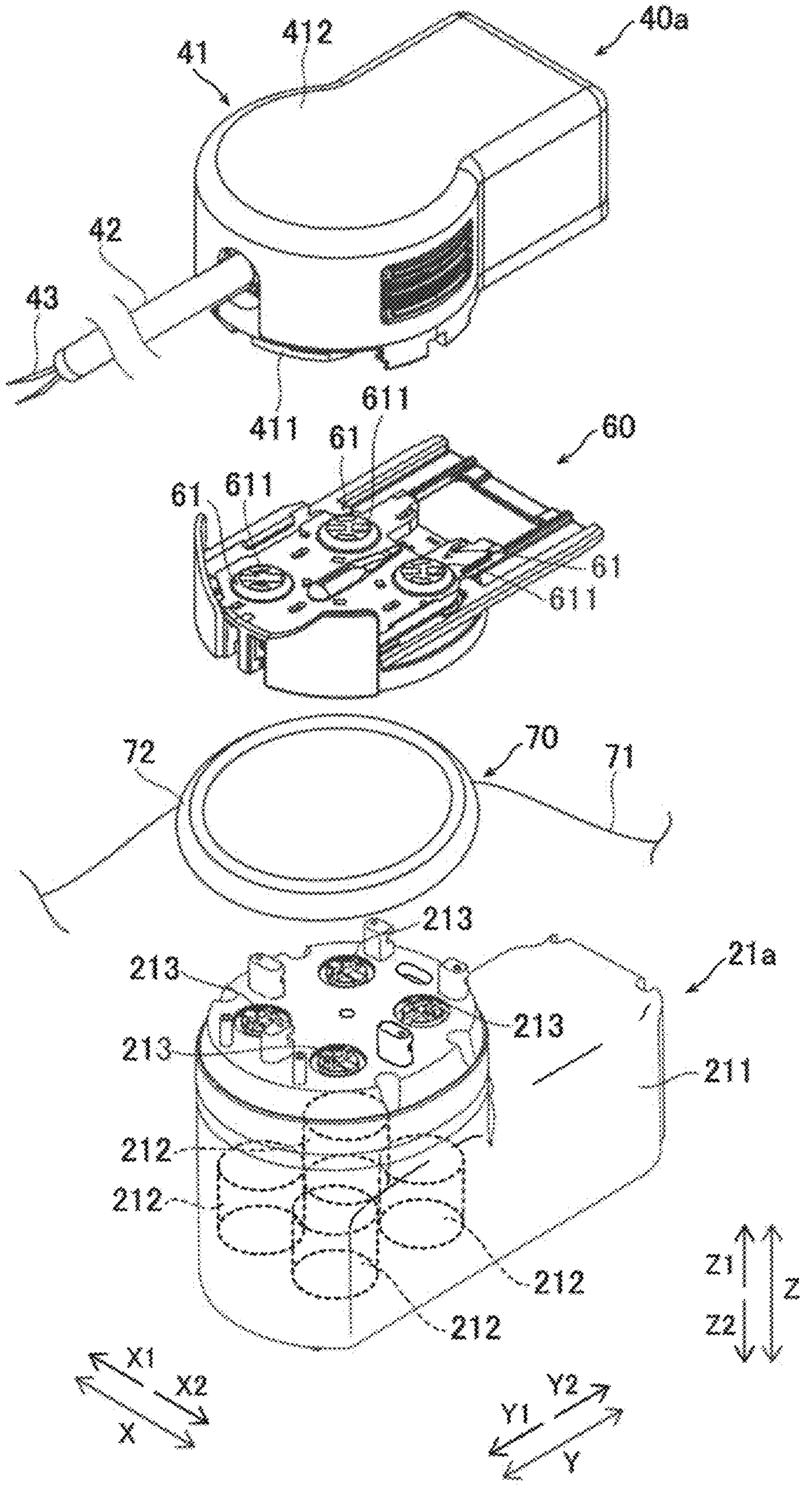
FIG. 4 is a diagram illustrating an exploded perspective view of a state where the surgical instrument according to of an embodiment is attached to the robot arm through the adaptor.
Figure 5:
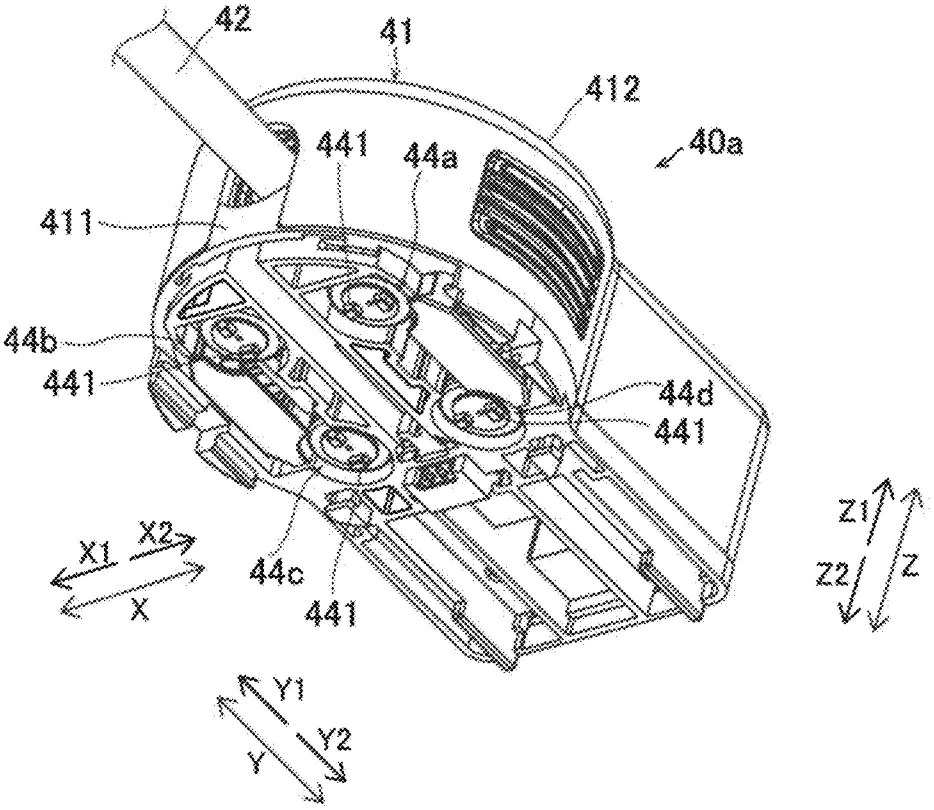
FIG. 5 is a diagram illustrating a perspective view of the surgical instrument according to an embodiment as seen from below.
Figure 6:
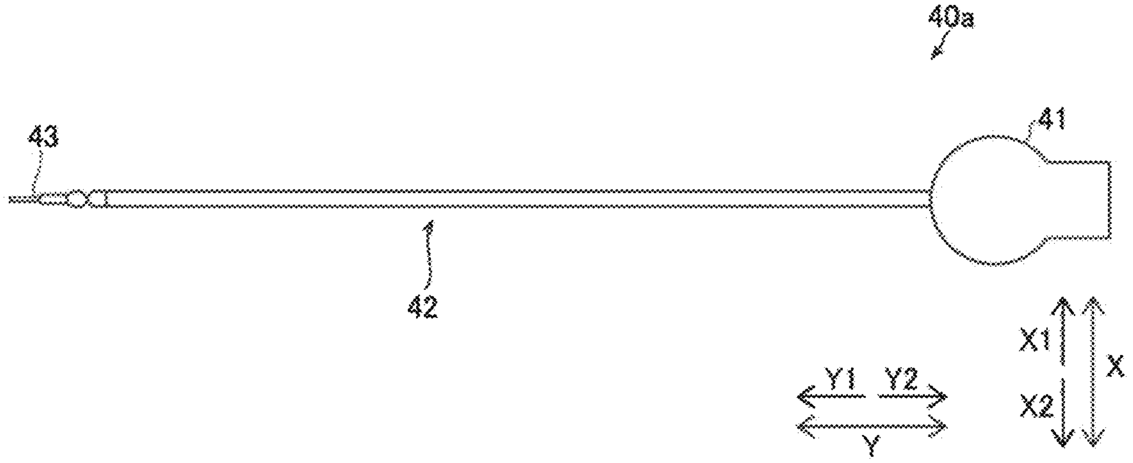
FIG. 6 is a diagram illustrating a plan view of the surgical instrument according to an embodiment.

With reference to FIGS. 3 to 5, configurations of the surgical instrument 40*a*, an adaptor 60, a drape 70, and the robot arm 21*a* are described.

Here, a longitudinal direction of the surgical instrument 40*a* (a longitudinal direction of the shaft 42) is defined as the Y direction, the distal side (the side toward the end effector 43) of the surgical instrument 40*a* along the Y direction is defined as the Y1 direction, and the opposite side of the Y1 direction is defined as the Y2 direction. The direction in which the surgical instrument 40*a* and the adaptor 60 are adjacent to each other is defined as a Z direction, the surgical instrument 40*a* side along the Z direction is defined as a Z1 direction, and the opposite side of the Z1 direction is defined as a Z2 direction. Further, the direction orthogonal to the Y direction and the Z direction is referred to as an X direction, one side along the X direction is referred as an X1 direction, and the other side along the X direction is referred to as an X2 direction.

As illustrated in FIGS. 3 and 4, the surgical instrument 40*a* is detachably attached to the robot arm 21*a* of the robotic surgical system 100. Specifically, the surgical instrument 40*a* is detachably attached to the robot arm 21*a* via the adaptor 60. The adaptor 60 is a drape adaptor configured to sandwich a sterile drape 70 to cover the robot arm 21*a*, in conjunction with the robot arm 21*a*.

The surgical instrument 40*a* is attached to the Z1 side of the adaptor 60. The adaptor 60 is attached to the Z1 side of the robot arm 21*a*.

As illustrated in FIG. 4, the drape 70 includes a body section 71 that covers the robot arm 21*a* and an attachment section 72 sandwiched between the robot arm 21*a* and the adaptor 60. The body section 71 is made of a flexible film member. The body section 71 includes an opening so that the robot arm 21*a* is engaged with the adaptor 60. To the opening of the body section 71, the attachment section 72 is provided. The attachment section 72 is made of a resin mold member. The attachment section 72 is harder (less flexible) than the body section 71. The attachment section 72 includes an opening so that the robot arm 21*a* is engaged with the adaptor 60.

Figure 7:
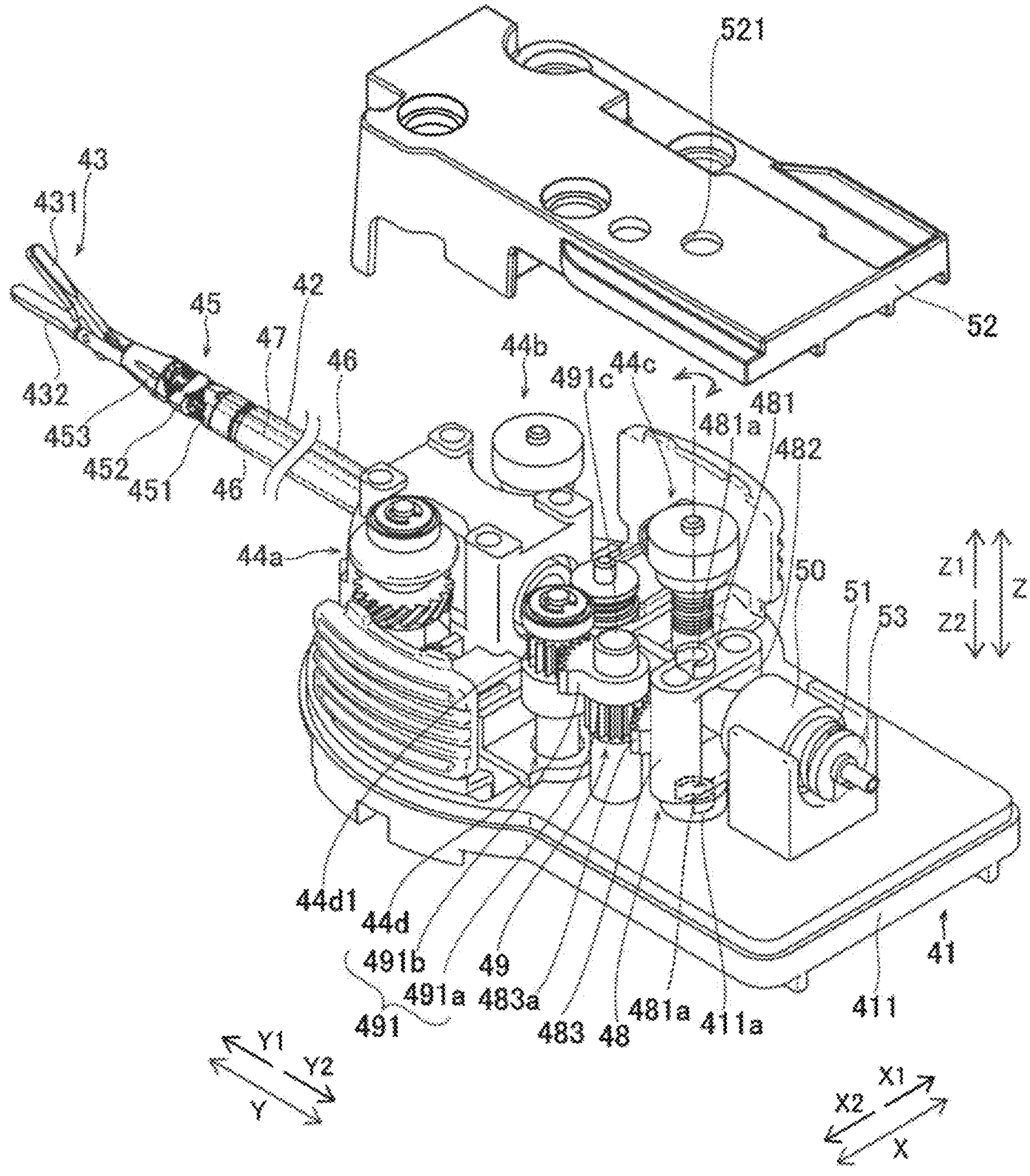
FIG. 7 is a diagram illustrating a perspective view of a state where a lid part of the surgical instrument according to an embodiment is detached.

As illustrated in FIGS. 5 and 7, the surgical instrument 40*a* includes a plurality (four) of drive shafts 44*a*, 44*b*, 44*c* and 44*d*. The drive shafts 44*a*, 44*b*, 44*c*, and 44*d* are provided within the housing 41 and are rotatable about respective rotation axes thereof extending along the Z axis. The drive shafts 44*a* to 44*d* are rotationally driven by driving forces from motors of drivers 212 (driving devices 212) provided in the robot arm 21*a*. The drive shafts 44*a* to 44*d* are provided for operating (driving) the elongate shaft 42, the end effector 43, and a wrist joint 45 (described later).

The drive shafts 44*a* to 44*d* respectively include protrusions 441 engaged with corresponding drive transmission members 61 (described later) of the adaptor 60 so as to transmit the driving forces from the robot arm 21*a* to the shaft 42, the end effector 43, and the wrist joint 45. The protrusions 441 protrude from the Z2 side surfaces of the drive shafts 44*a* to 44*d* toward the adaptor 60 (the Z2 side). Each of the protrusion 441 includes plural protrusion portions that arranged in a straight line.

As illustrated in FIG. 4, the adaptor 60 includes the drive transmission members 61. The drive transmission members 61 are configured to transmit the driving forces from the robot arm 21*a* to the drive shafts 44*a* to 44*d* of the surgical instrument 40*a*. In other words, the drive transmission members 61 respectively provided to correspond to the drive shafts 44*a* to 44*d* of the surgical instrument 40*a*. The drive transmission members 61 are rotatable about respective rotation axes thereof, which extend along the Z direction.

The drive transmission members 61 include engagement recesses 611 that are respectively engaged with the protrusions 441 of the drive shafts 44*a* to 44*d* of the surgical instrument 40*a*. The engagement recess 611 is located on the surgical instrument 40*a* side (the Z1 side) of the drive transmission member 61 and is recessed from the Z1 side surface of the drive transmission member 61 toward the Z2 side, opposite to the surgical instrument 40*a* side. Each of the drive transmission members 61 further includes an engagement recess provided on the Z2 side surface thereof and is configured to be engaged with a corresponding engagement protrusion 213 (described later) of the robot arm 21*a*.

The robot arm 21*a* includes a frame 211, the drivers 212, and the engagement protrusions 213. The plural (four) drivers 212 are provided to correspond to the plural drive shafts 44*a* to 44*d* of the surgical instrument 40*a* and correspond to the plural drive transmission members 61 of the adaptor 60. Each of the drivers 212 includes an absolute encoder and a servomotor and is configured to drive the corresponding engagement protrusion 213 to rotate about rotational axes thereof extending in the Z direction. The engagement protrusion 213 of the driver 212 is engaged with the engagement recess provided on the Z2 side surface of the corresponding drive transmission member 61. The drivers 212 are configured to drive the drive transmission members 61 of the adaptor 60, which are respectively engaged with the engagement protrusions 213 of the drivers 212, to rotate about the rotational axes of the drive transmission members 61 extending in the Z direction, so as to drive the drive shafts 44*a* to 44*d* of the surgical instrument 40*a*, which are respectively engaged with the drive transmission members 61, to rotate about the rotational axes of the drive shafts 44*a* to 44*d* extending in the Z direction.

(Detailed Configuration of Surgical Instrument)

With reference to FIGS. 6 to 26, the configuration of the surgical instrument 40*a* is described in detail below.

As illustrated in FIGS. 6 to 26, the surgical instrument 40*a* includes the housing 41, the elongate shaft 42, the end effector 43, and the plural drive shafts 44*a* to 44*d*. The surgical instrument 40*a* also includes the wrist joint 45, wires 46, a rod 47, a lever 48, a driving force transmission part 49, a holding member 50 (a retainer 50), and a spring member 51. Note that the rod 47 is an example of an elongate element.

As illustrated in FIG. 7, the housing 41 includes a base 411 and a lid part 412 (see FIG. 4). The base 411 is attached to the robot arm 21*a* (see FIG. 4) via the adaptor 60. The base 411 is provided with the plural drive shafts 44*a* to 44*d*. The lid part 412 removably covers the base 411. Specifically, the lid part 412 covers the base 411 from the side (the Z1 side) opposite to a mounting surface of the base 411 to the robot arm 21*a*.

The shaft 42 is provided to extend in the Y direction. A proximal end (an end on the Y2 side) of the shaft 42 is connected to the base 411. A distal end (an end on the Y1 side) of the shaft 42 is connected to a proximal end of the wrist joint 45.

The end effector 43 is connected to a distal end of the wrist joint 45. The end effector 43 includes a first jaw 431 and a second jaw 432.

Figure 8:
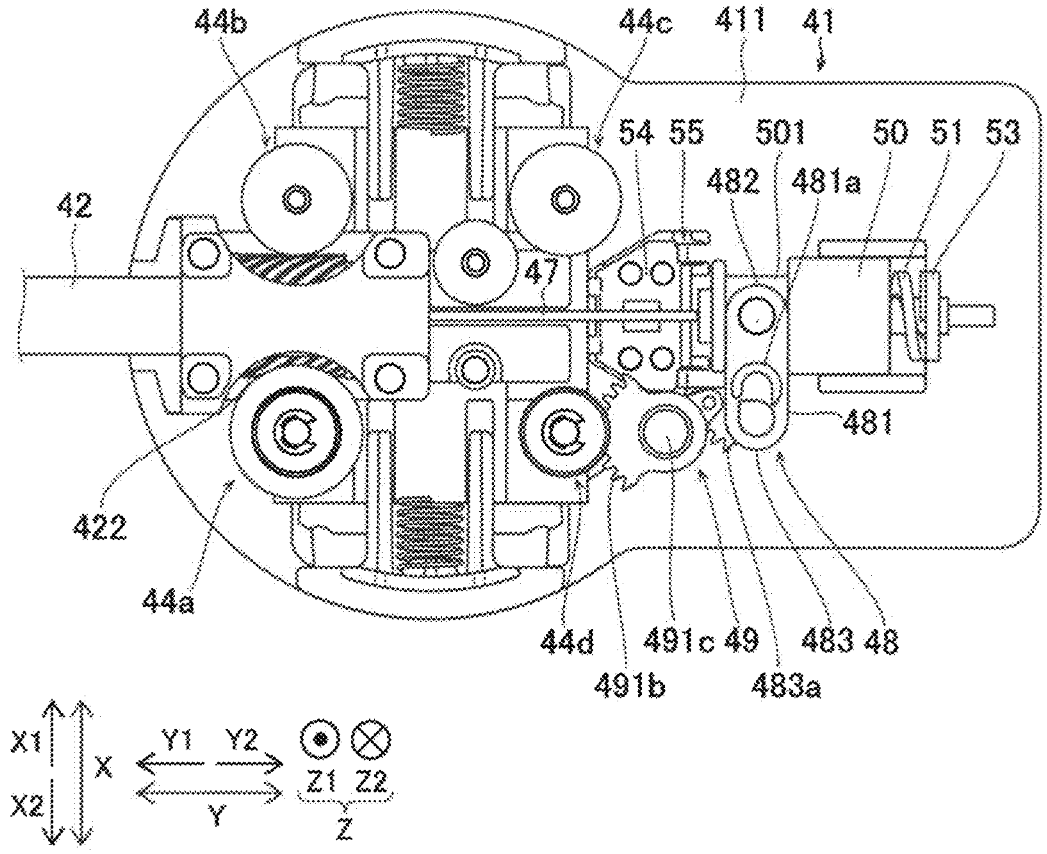
FIG. 8 is a diagram illustrating a plan view of the state where the lid part of the surgical instrument according to an embodiment is detached.
Figure 9:
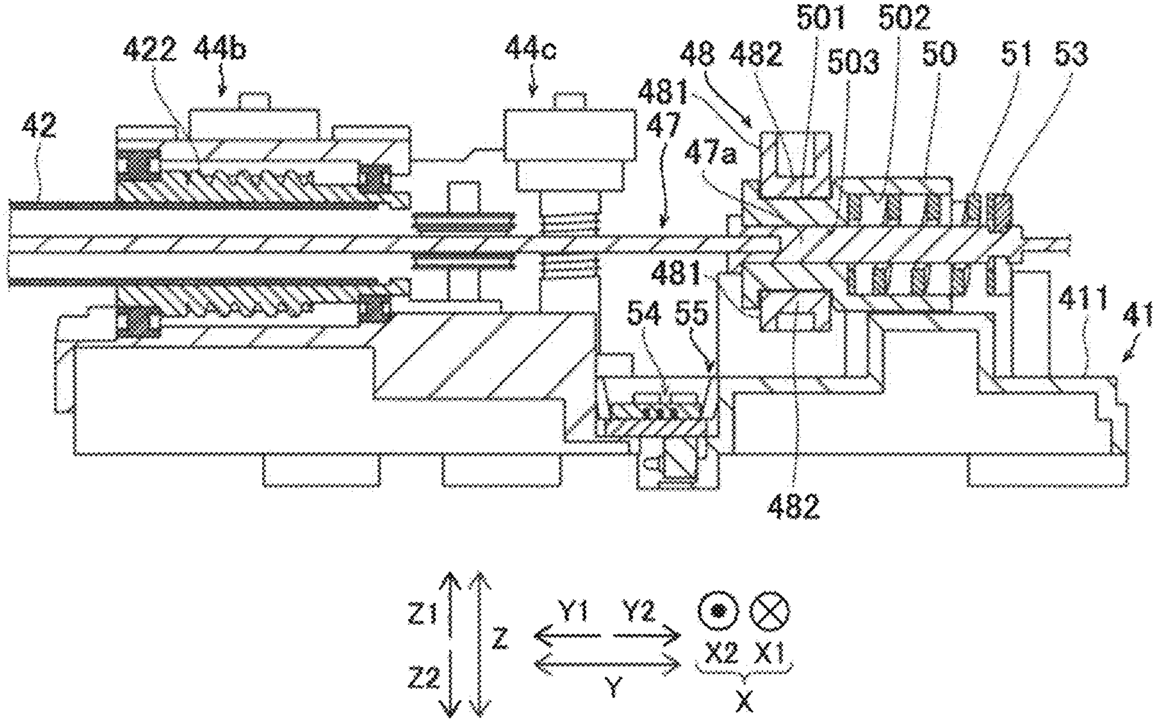
FIG. 9 is a diagram illustrating a cross-sectional view of the state where the lid part of the surgical instrument according to an embodiment is detached.

As illustrated in FIGS. 7 to 9, the drive shafts 44*a* to 44*d* include a first drive shaft 44*a* for rolling the elongate shaft 42 about an axis thereof extending in the Y direction, a second drive shaft 44*b* and a third drive shaft 44*c* for pitching a first joint 45*a* about a rotation axis A1 and yawing a second joint 45*b* about a rotation axis A2, and a fourth drive shaft 44*d* for moving the rod 47 in the Y direction.

The first drive shaft 44*a* is connected to a gear 422 that is connected to the proximal end of the shaft 42. When the first drive shaft 44*a* is driven to rotate, the elongate shaft 42 is driven to rotate in a rolling manner by the first drive shaft 44*a* via the gear 422. The second drive shaft 44*b* and the third drive shaft 44*c* are connected to the wires 46 that are connected to the wrist joint 45. When the second drive shaft 44*b* and the third drive shaft 44*c* are driven to rotate, the wrist joint 45 is caused to perform pitch or yaw joint motion via the wires 46. Note that the movement of the rod 47 in the Y direction by the fourth drive shaft 44*d* will be described later.

Figure 10:
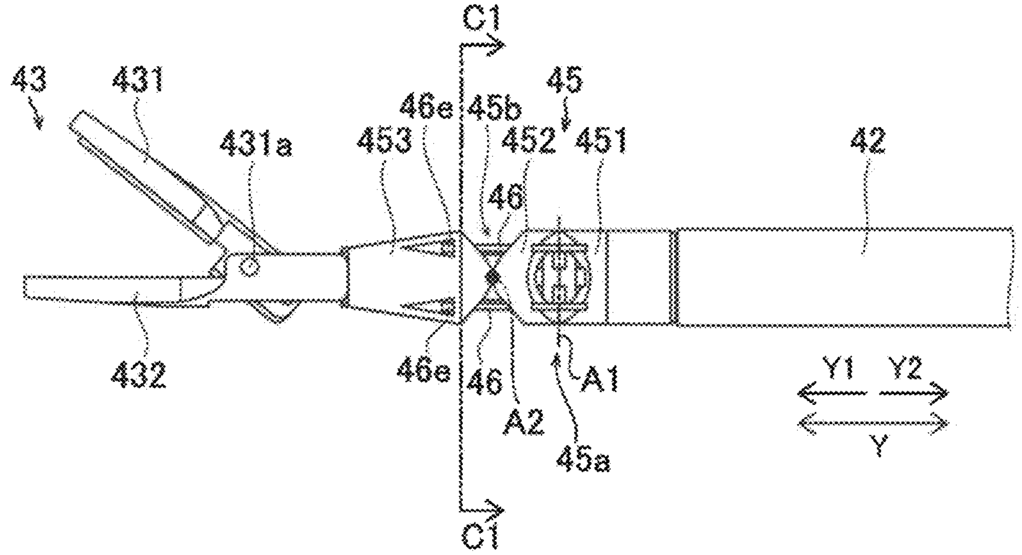
FIG. 10 is a diagram illustrating a side view of an end effector, a wrist joint and a shaft according to an embodiment.
Figure 11:
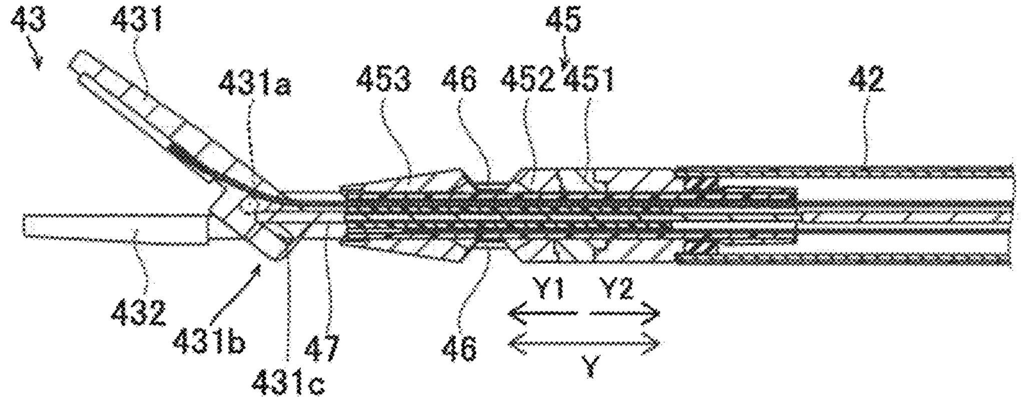
FIG. 11 is a diagram illustrating a cross-sectional view of the end effector, the wrist joint, and the shaft according to an embodiment.

As illustrated in FIGS. 7, 10 and 11, the wrist joint 45 is connected to the distal end side (Y1 side) of the shaft 42 and is configured to articulate with respect to the shaft 42. Specifically, the wrist joint 45 includes a first joint component 451, a second joint component 452, and a third joint component 453. The first joint component 451 is connected to the distal end side (Y1 side) of the shaft 42. The second joint component 452 is connected to the first joint component 451 via the first joint 45*a*. The second joint component 452 is disposed on the distal end side (Y1 side) of the first joint component 451, and is meshed with the first joint component 451 so as to perform a pitch joint movement. The third joint component 453 is connected to the second joint component 452 via the second joint 45*b*. The third joint component 453 is disposed on the distal end side of the second joint component 452 and is meshed with the second joint component 452 so as to perform a yaw joint movement. The third joint component 453 has a shape whose diameter gradually decreases toward the distal end side (Y1 side) in order to connect the shaft 42 and the end effector 43 which has a smaller diameter than that of the shaft 42. The wrist joint 45 will be described in detail later. Note that the first joint component 451, the second joint component 452, and the third joint component 453 are examples of a first joint component, a second joint component, and a third joint component, respectively.

The wires 46 are provided to drive the wrist joint 45. The wires 46 allow the wrist joint 45 to perform the pitch and yaw joint movements. The wires 46 are provided inside the shaft 42 and extend in the Y direction and the number of the wires 46 provided is four. Two of the four wires 46 connect the wrist joint 45 and the second drive shaft 44*b* to each other, and the other two of the four wires 46 connect the wrist joint 45 and the third drive shaft 44*c* to each other.

Figure 12:
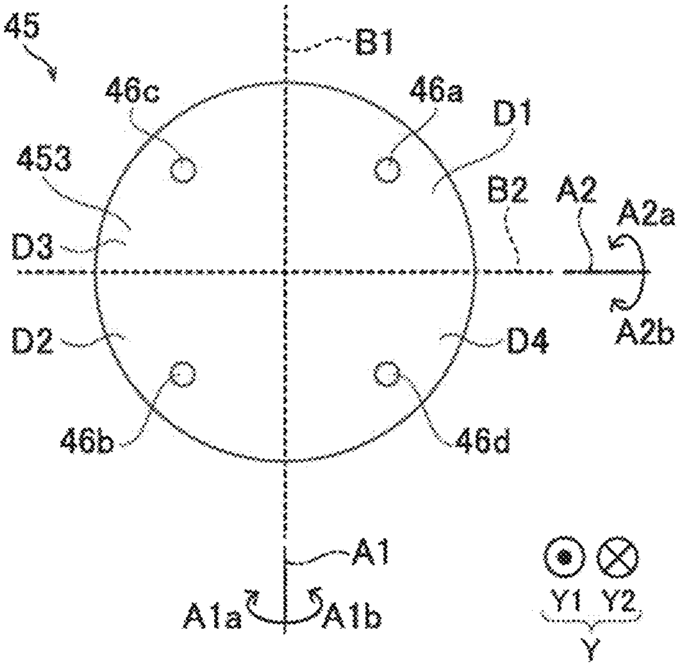
FIG. 12 is a diagram illustrating a cross-sectional view of a third joint component taken along the arrow C1-C1 in FIG. 10.

For example, as illustrated in FIG. 12, the four wires 46 include wires 46*a*, 46*b*, 46*c*, and 46*d*. The wires 46*a*, 46*b*, 46*c* and 46*d* have distal ends thereof fixed to the third joint component 453. Proximal ends of the wires 46*a* and 46*b* are wound around and fixed to the second drive shaft 44*b*. The wires 46*a* and 46*b* are wound around the second drive shaft 44*b* in opposite directions. In other words, when the second drive shaft 44*b* rotates in one direction, one of the wires 46*a* and 46*b* is pulled in the proximal direction (Y2 direction), and the other of the wires 46*a* and 46*b* is released and pulled out in the distal direction (Y1 direction). To the contrary, when the second drive shaft 44*b* rotates in the other direction opposite to the one direction, the other of the wires 46*a* and 46*b* is pulled in the proximal direction (Y2 direction), and the one of the wires 46*a* and 46*b* is released and pulled out in the distal direction (Y1 direction). Note that the wires 46*a*, 46*b*, 46*c*, and 46*d* are examples of a first wire, a second wire, a third wire, and a fourth wire, respectively.

Proximal ends of the wires 46*c* and 46*d* are wound around and fixed to the third drive shaft 44*c*. The wires 46*c* and 46*d* are wound around the third drive shaft 44*c* in opposite directions. In other words, when the third drive shaft 44*c* rotates in one direction, one of the wires 46*c* and 46*d* is pulled in the proximal direction (Y2 direction), and the other of the wires 46*c* and 46*d* is released and pulled out in the distal direction (Y1 direction). To the contrary, when the third drive shaft 44*c* rotates in the other direction opposite to the one direction, the other of the wires 46*c* and 46*d* is pulled in the proximal direction (Y2 direction), and the one of the wires 46*c* and 46*d* is released and pulled out in the distal direction (Y1 direction).

As illustrated in FIG. 10, the wrist joint 45 includes the first joint 45*a* that rotates (pitches) about the rotation axis A1 orthogonal to the longitudinal direction of the shaft 42 so as to perform the pitch joint movement, and the second joint 45*b* that rotates (yaws) about the rotation axis A2 orthogonal to the longitudinal direction of the shaft 42 and the rotation axis A1 so as to perform the yaw joint movement. The wires 46 cause the wrist joint 45 to pitch and yaw, by driving the wires 46*a* and 46*b* by the second drive shaft 44*b* and by driving the wires 46*c* and 46*d* by the third drive shaft 44*c*. The wrist joint 45 is driven by the second drive shaft 44*b* and the third drive shaft 44*c* to perform the rotation (the pitch joint movement) about the rotation axis A1 of the first joint 45*a* and the rotation (the yaw joint movement) about the rotation axis A2 of the second joint 45*b*. The second drive shaft 44*b* is configured to rotate in a first direction to apply tension to the wire 46*a* and to rotate in a second direction opposite the first direction to apply tension to the wire 46*b*. The third drive shaft 44*c* is configured to rotate in a third direction to apply tension to the wire 46*c*, and to rotate in a fourth direction opposite to the third direction to apply tension to the wire 46*d*. When the rotation of the second drive shaft 44*b* applies the tension to the wire 46*a* and the rotation of the third drive shaft 44*c* applies the tension to the wire 46*d*, or when the rotation of the second drive shaft 44*b* applies the tension to the wire 46*b* and the rotation of the third drive shaft 44*c* applies the tension to the wire 46*c*, the first joint 45*a* performs the pitch joint movement about the rotation axis A1. When the rotation of the second drive shaft 44*b* applies the tension to the wire 46*a* and the rotation of the third drive shaft 44*c* applies the tension the wire 46*c*, or when the rotation of the second drive shaft 44*b* applies the tension to the wire 46*b* and the rotation of the third drive shaft 44*c* applies the tension to the wire 46*d*, the second joint 45*b* performs the yaw joint movement about the rotation axis A2. Note that the rotation axis A1 and the rotation axis A2 are examples of a rotation axis A1 and a rotation axis A2, respectively.

Specifically, as illustrated in FIG. 12, when the wire 46*a* is pulled and the wire 46*b* is loosened by the second drive shaft 44*b* and the wire 46*d* is pulled and the wire 46*c* is loosened by the third drive shaft 44*c*, the first joint 45*a* rotates in the A1*b* direction about the rotation axis A1. Further, when the wire 46*b* is pulled and the wire 46*a* is loosened by the second drive shaft 44*b* and the wire 46*c* is pulled and the wire 46*d* is loosened by the third drive shaft 44*c*, the first joint 45*a* rotates in the Ala direction about the rotation axis A1.

To the contrary, when the wire 46*a* is pulled and the wire 46*b* is loosened by the second drive shaft 44*b* and the wire 46*c* is pulled and the wire 46*d* is loosened by the third drive shaft 44*c*, the second joint 45*b* rotates in the A2*a* direction about the rotation axis A2. Further, when the wire 46*b* is pulled and the wire 46*a* is loosened by the second drive shaft 44*b* and the wire 46*d* is pulled and the wire 46*c* is loosened by the third drive shaft 44*c*, the second joint 45*b* rotates in the A2*b* direction about the rotation axis A2.

The four wires 46*a* to 46*d* have respective ends 46*e* (see FIG. 10) fixed to the third joint component 453 at the vicinity of the proximal end of the third joint component 453. FIG. 12 is a cross-sectional view of the third joint component 453 taken along the line C1-C1 of FIG. 10. As illustrated in FIG. 12, a cross section of the third joint component 453 includes four regions, which are a first region D1 to a fourth region D4, divided by a plane B1 parallel to both the longitudinal direction (Y direction) of the shaft 42 and the rotation axis A1, and a plane B2 parallel to both the longitudinal direction (Y direction) of the shaft 42 and the rotation axis A2. The four wires 46*a* to 46*d* pass through the first region D1 to the fourth region D4, respectively, and have the ends 46*e* thereof fixed to the vicinity of the proximal end of the third joint component 453. Specifically, the wire 46*a* passes through the first region D1 at a position offset from planes B1 and B2, the wire 46*b* passes through the second region D2 at a position offset from planes B1 and B2, the wire 46*c* passes through the third region D3 at a position offset from planes B1 and B2, and the wire 46*d* passes through the fourth region D4 at a position offset from planes B1 and B2. As illustrated in FIG. 12, the first region D1 is arranged in a first quadrant, the second region D2 is arranged in a third quadrant, the third region D3 is arranged in a second quadrant, and the fourth region D4 is arranged in a fourth quadrant. Note that the plane B1 and the plane B2 are examples of a first plane and a second plane, respectively.

As illustrated in FIGS. 7 to 9 and 11, the rod 47 is provided for driving the end effector 43. The rod 47 is provided inside the shaft 42 and extends along the Y direction in the shaft 42. A distal end of the rod 47 is connected to the end effector 43. Specifically, the distal end of the rod 47 is connected to the first jaw 431.

Figure 13:
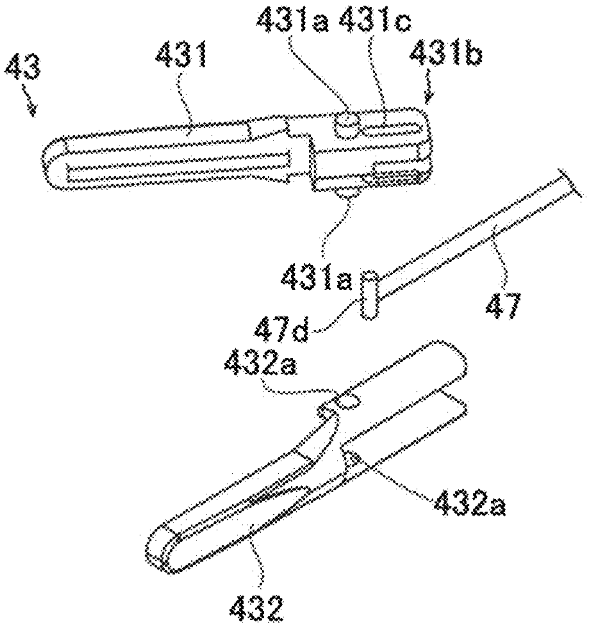
FIG. 13 is a diagram illustrating an exploded perspective view of the end effector and a rod according to an embodiment.
Figure 14:
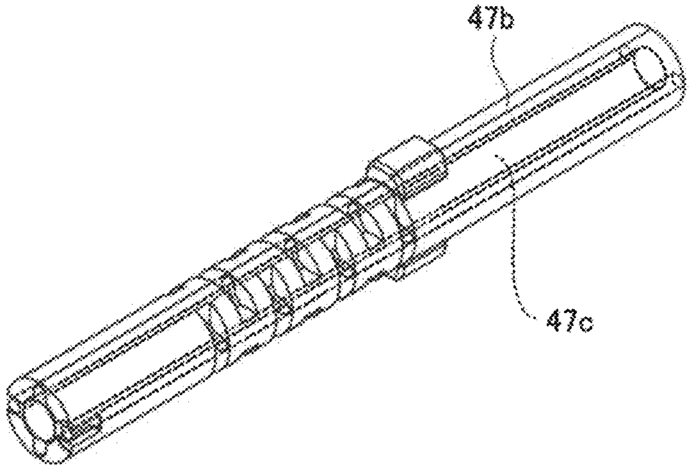
FIG. 14 is a diagram illustrating a perspective view of a guide portion in the wrist joint of the surgical instrument according to an embodiment.

As illustrated in FIGS. 11 and 13, the first jaw 431 includes a support shaft 431*a* that is rotatably supported by the second jaw 432 and a connection portion 431*b* that is connected to the distal end of the rod 47, such that the first jaw 431 rotates about an axis of the support shaft 431*a* due to the movement of the rod 47 in the Y direction. With this configuration, the first jaw 431 is rotated about the axis of the support shaft 431*a* by moving the rod 47 in the Y direction, so that the first jaw 431 is opened or closed relative to the second jaw 432. The end effector 43 is of a single-opening type in which the first jaw 431 opens and closes relative to the second jaw 432.

The support shaft 431*a* includes a pair of shaft portions that are provided on both sides of the first jaw 431. The pair of shaft portions of the support shaft 431*a* are inserted in and rotatably supported by a pair of holes 432*a* provided to the second jaw 432. The connection portion 431*b* includes a long hole portion 431*c*. The long hole portion 431*c* includes a pair of long holes 431*c*. A pin portion 47*d* is provided at the distal end of the rod 47 and extends in a direction orthogonal to the Y direction. One end and the other end of the pin portion 47*d* of the rod 47 are inserted in and supported by the pair of long holes 431*c* of the connection portion 431*b* of the first jaw 431 so that the pin portion 47*d* of the rod 47 is slidable along the long holes 431*c* of the connection portion 431*b* of the first jaw 431. When the rod 47 is moved in the Y1 direction, the pin portion 47*d* of the rod 47 slides along the long holes 431*c*, so that a force is applied in a direction in which the first jaw 431 opens. As a result, the first jaw 431 rotates about the axis of the support shaft 431*a* in the opening direction of the first jaw 431. To the contrary, when the rod 47 is moved in the Y2 direction, the pin portion 47*d* of the rod 47 slides along the long holes 431*c*, so that a force is applied in a direction in which the first jaw 431 closes. As a result, the first jaw 431 rotates about the axis of the support shaft 431*a* in the closing direction.

At the wrist joint 45, the rod 47 needs to bend as the wrist joint 45 articulates. Accordingly, the rod 47 is guided by a guide portion 47*b* provided to the wrist joint 45 as illustrated in FIG. 13. Specifically, a part of the rod 47 that passes through the wrist joint 45 is made of a wire 47*c* and is configured to be bendable. The guide portion 47*b* is made of resin and is configured to be bendable. The guide portion 47*b* guides the movement of the wire 47*c* along the Y direction so as to prevent the wire 47*c* from buckling. This allows the force generated by the movement of the rod 47 in the Y direction to be transmitted with preventing the force from losing.

In an embodiment, as illustrated in FIGS. 7 to 9, the lever 48 moves the rod 47 in the Y direction. The lever 48 includes an arm 481, an engagement portion 482 provided to one side of the arm 481 and engaged with the rod 47, and a shaft portion 481*a* that is provided to the other side of the arm 481 and is rotatably arranged on the base 411 so as to move the engagement portion 482 by the driving force from the fourth drive shaft 44*d*. In other words, the lever 48 includes the shaft portion 481*a* that rotates about an axis thereof by the driving force from the fourth drive shaft 44*d*, the arm 481 provided to the shaft portion 481*a*, and the engagement portion 482 provided to the arm 481 and engaged with the rod 47. With this configuration, the shaft portion 481*a* of the lever 48, which moves the rod 47 in the Y direction, serves as the rotation axis of the lever 48, so there is no need to use one of the drive shafts as the rotation axis of the lever. As a result, the rod 47 can be moved in the Y direction of the shaft 42 using only one drive shaft (e.g., the fourth drive shaft 44*d*), to operate the end effector 43. As a result, the four drive shafts 44*a* to 44*d* can rotate the elongate shaft 42 in roll, articulate the end effector 43 in pitch and yaw, and also move the rod 47 in the Y direction of the shaft 42 for operating the end effector 43.

In an embodiment, the arm 481 of the lever 48 includes a pair of arms 481 opposed to each other in the Z direction. The pair of arms 481 include a Z1 side arm 481, and a Z2 side arm 481 that is opposes to the Z1 side arm 481 in the Z direction. The engagement portion 482 of the lever 48 includes a Z1 side engagement portion 482 provided to the Z1 side arm 481 and a Z2 side engagement portion 482 provided to the Z2 side arm 481. The Z1 side engagement portion 482 is engaged with the rod 47 from one side (the Z1 side). The Z2 side engagement portion 482 is engaged with the rod 47 from the other side (the Z2 side). This allows the engagement portions 482 to be engaged with the rod 47 from the one side and the other side of the rod 47, so that the driving force of the fourth drive shaft 44*d* can be reliably transmitted to the rod 47 via the lever 48. Note that the Z1 side arm 481 and the Z2 side arm 481 are examples of a first arm and a second arm, respectively. The Z1 side engagement portion 482 and the Z2 side engagement portion 482 are examples of a first engagement portion and a second engagement portion, respectively.

In an embodiment, the Z1 side engagement portion 482 is engaged with the rod 47 from the one side (the Z1 side) via the holding member 50. The Z2 side engagement portion 482 is engaged with the rod 47 from the other side (the Z2 side) via the holding member 50. With this configuration, the engagement portions 482 are engaged with the rod 47 from the one side and the other side of the rod 47 via the holding member 50, so there is no need to provide, to the rod 47, an engagement portion(s) to be engaged with the engagement portions 482. As a result, the structure of the rod 47 can be simplified.

The pair of arms 481 are spaced apart from each other in the Z direction and connected to each other by a connection portion 483 extending in the Z direction. Each of the pair of arms 481 is provided to extend in the X direction from the connection portion 483 to the position of the rod 47. Each of the pair of arms 481 includes a shaft portion 481*a* between an end thereof on the connection portion 483 side and an end thereof on the rod 47 side. Specifically, each arm 481 includes the shaft portion 481*a* at a position closer to the connection portion 483 from the center between the connection portion 483 side end portion and the rod 47 side end portion of the arm 481. The rod 47 side end portion of each arm 481 is provided with the engagement portion 482.

The engagement portion 482 of one of the pair of arms 481 protrudes toward the Z2 side and is engaged with an engagement portion 501 (described later) of the holding member 50 from the Z1 side. The engagement portion 482 of the other of the pair of arms 481 protrudes toward the Z1 side and is engaged with the engagement portion 501 of the holding member 59 from the Z2 side.

Further, the shaft portion 481*a* of one of the pair of arms 481 protrudes toward the Z1 side. The shaft portion 481*a* of the one of the pair of arms 481 is rotatably supported by a frame member 52 (see FIG. 7) provided inside the housing 41. Specifically, the shaft portion 481*a* of the one of the pair of arms 481 is inserted in and is rotatably supported by a support portion 521 including a hole provided in the frame member 52. The shaft portion 481*a* of the other of the pair of arms 481 protrudes toward the Z2 side. The shaft portion 481*a* of the other of the pair of arms 481 is rotatably supported by the base 411. Specifically, the shaft portion

481*a* of the other of the pair of arms 481 is inserted in and rotatably supported by a support portion 411*a* including a recess provided in the base 411.

In an embodiment, the axis of the shaft portions 481*a* is disposed between the engagement portion 482 and the fourth drive shaft 44*d* in the X direction orthogonal to the Y direction. This allows the axis of the shaft portions 481*a* to be positioned between the engagement portion 482 and the fourth drive shaft 44*d* in the direction orthogonal to the Y direction, making the lever 48 more compact than in a case where the axis of the shaft portions 481*a* is positioned on the outer side of the fourth drive shaft 44*d*. The axis of the shaft portions 481*a* is disposed on the fourth drive shaft 44*d* side in the X direction from the center between the engagement portion 482 and the fourth drive shaft 44*d*.

In an embodiment, the driving force transmission part 49 is provided between the fourth driving shaft 44*d* and the lever 48, and transmits the driving force from the fourth driving shaft 44*d* to the lever 48. This allows the driving force to be transmitted from the fourth drive shaft 44*d* to the lever 48 via the driving force transmission part 49, so that the lever 48 can be disposed away from the fourth drive shaft 44*d*. As a result, even in cases where it is difficult to secure a space for providing the lever 48 near the fourth drive shaft 44*d*, the space for providing the lever 48 can be easily secured.

In an embodiment, the driving force transmission part 49 includes a gear train 491 including a spur gear 491*a* and a sector gear 491*b*, and transmits the driving force from the fourth drive shaft 44*d* to the lever 48 by the gear train 491. This allows the driving force to be reliably transmitted from the fourth drive shaft 44*d* to the lever 48 by the gear train 491, which transmits the driving force through meshing. Further, since the gear train 491 includes the sector gear 491*b*, the gear train 491 can be made more compact than in a case where a spur gear is provided instead of the sector gear 491*b*.

In an embodiment, the driving force transmission part 49 transmits the rotation of the fourth drive shaft 44*d* to the lever 48 with decelerating the speed of the rotation of the fourth drive shaft 44*d*. As a result, the lever 48 is driven with a torque that increases inversely proportional to the deceleration of the rotation of the fourth drive shaft 44*d*, so that the rod 47 can be easily moved in the Y direction by driving the lever 48. In addition, the driving of the lever 48 by the torque that increases inversely proportional to the deceleration of the rotation of the fourth drive shaft 44*d* is effective in the case where the spring member 51 is provided as in an embodiment.

The sector gear 491*b* meshes with a spur gear 44*d*1 provided to the fourth drive shaft 44*d*. The sector gear 491*b* has the number of teeth that reduces the rotation speed of the fourth drive shaft 44*d*. The spur gear 491*a* meshes with a sector gear 483*a* provided to the connection portion 483 of the lever 48. The spur gear 491*a* and the sector gear 491*b* are supported by a common rotation shaft 491*c* and rotate integrally with each other by the rotation shaft 491*c*.

In an embodiment, the holding member 50 holds the rod 47. The spring member 51 biases the holding member 50 toward the distal end side (Y1 side) in the Y direction. The engagement portions 482 are engaged with the rod 47 via the holding member 50, and when the engagement portions 482 push the holding member 50 toward the proximal end side (Y2 side) in the Y direction, a gripping force of the end effector 43 is generated by the reaction force of the spring member 51. Accordingly, it is possible to determine the gripping force of the end effector 43 by a spring constant of the spring member 51, so that the gripping force of the end effector 43 can be applied stably. Also, unlike a case where the gripping force of the end effector 43 is applied using a wire(s) as in the wrist joint 45, the gripping force is less susceptible to slight stretching of the wire. This eliminates the need to precisely set the tightening angles of the motors of the drivers 212.

The holding member 50 includes the engagement portion 501, a spring accommodation portion 502, and a rod holding portion 503. The engagement portion 501 of the holding member 50 is engaged with the engagement portions 482 of the lever 48. The engagement portion 501 is configured as a recess formed in a circumferential shape. A portion of the engagement portion 501 on the Z1 side is recessed toward the Z2 side, and is engaged with the engagement portion 482 of one of the pair of arms 481. A portion of the engagement portion 501 on the Z2 side is recessed toward the Z1 side, and is engaged with the engagement portion 482 of the other of the pair of arms 481. The spring accommodation portion 502 accommodates the spring member 51. The spring accommodation portion 502 includes a recess recessed toward the Y1 side. The spring accommodation portion 502 holds the spring member 51 between the spring accommodation portion 502 and a plate-shaped washer 53 provided on the Y2 side of the spring accommodation portion 502. The rod holding portion 503 holds a held portion 47*a* provided to the rod 47. The rod holding portion 503 includes a hole extending along the Y direction.

The spring member 51 is a compression coil spring having a predetermined spring constant. When the holding member 50 is moved in the Y2 direction by the lever 48, the spring member 51 is compressed between the spring accommodation portion 502 and the washer 53. When the holding member 50 is moved in the Y1 direction by the lever 48, the spring member 51 is stretched between the spring accommodation portion 502 and the washer 53.

Next, the operation of moving the rod 47 in the Y direction by the lever 48 is described. When the fourth drive shaft 44*d* is driven to rotate, the driving force from the fourth drive shaft 44*d* is transmitted to the lever 48 via the gear train 491 of the driving force transmission part 49. This causes the lever 48 to rotate about the axis of the shaft portion 481*a* of the lever 48. In the case where the rod 47 is moved in the Y1 direction, a Y1 side surface of the engagement portion 482 of the lever 48 abuts against a Y2 side surface of the engagement portion 501 of the holding member 50, and the holding member 50 is pushed and moved in the Y1 direction. With this, the rod 47, whose held portion 47*a* is held by the rod holding portion 503 of the holding member 50, is moved in the Y1 direction. This moves the first jaw 431 in the opening direction. To the contrary, in the case where the rod 47 is moved in the Y2 direction, a Y2 side surface of the engagement portion 482 of the lever 48 abuts against a Y1 side surface of the engagement portion 501 of the holding member 50, and the holding member 50 is pushed and moved in the Y2 direction. With this, the rod 47, whose held portion 47*a* is held by the rod holding portion 503 of the holding member 50, is moved in the Y2 direction. This moves the first jaw 431 in the closing direction.

(Configuration of Mechanism for Fixing Memory Board)

Next, a configuration of a mechanism 55 for fixing a circuit board 54 is described with reference to FIGS. 8, 15, and 16.

Figure 15:
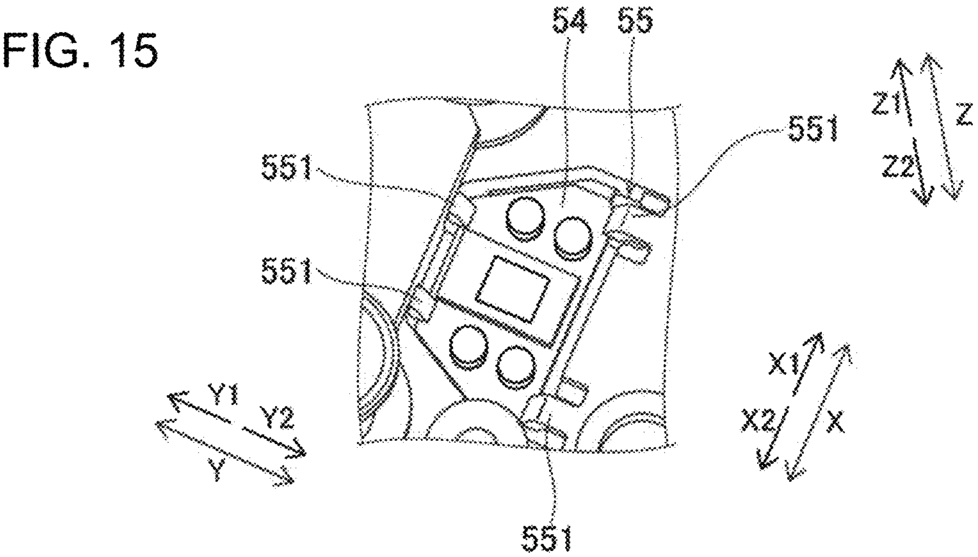
FIG. 15 is a diagram illustrating a perspective view of a memory board and a fixing portion according to an embodiment.
Figure 16:
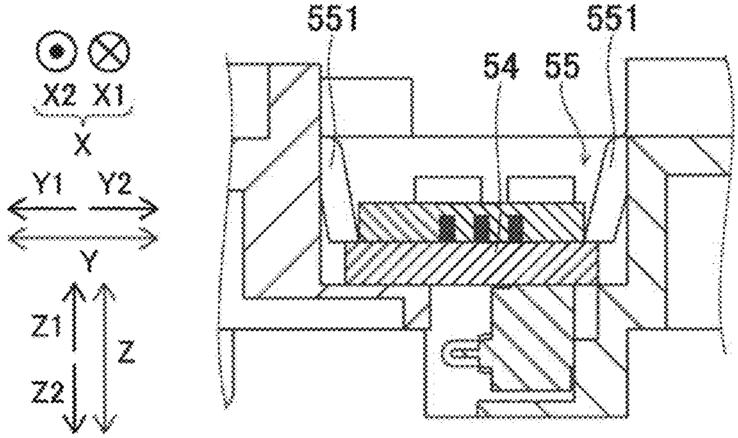
FIG. 16 is a diagram illustrating a cross-sectional view of the memory board and the fixing portion according to an embodiment.

As illustrated in FIGS. 8, 15 and 16, the surgical instrument 40*a* includes the circuit board 54 and the fixing mechanism 55 for fixing the circuit board 54. The circuit board 54 is provided on the base 411. The circuit board 54 is a memory board. The circuit board 54 stores information about the surgical instrument 40*a*, such as a type of the surgical instrument 40*a* and the number of times the surgical instrument 40*a* has been used. The fixing mechanism 55 fixes the circuit board 54 to the base 411. The fixing mechanism 55 is a snap-fit fixing mechanism with a plurality (four pieces) of snap-fit portions 551. The snap fit portions 551 are provided two on each of the Y1 side and the Y2 side of the circuit board 54, and press an outer periphery of the circuit board 54 from the Z1 side. When the circuit board 54 is attached to the fixing mechanism 55 from the Z1 side toward the Z2 side, the snap fit portions 551 are pressed by the circuit board 54 and elastically deformed. By providing the snap-fit mechanism as the fixing mechanism 55, it is possible to fix the circuit board 54 to the base 411 with a simple structure.

(Configuration of Wrist Joint)

Next, a configuration of the wrist joint 45 is described with reference to FIGS. 17 to 26.

Figure 17:
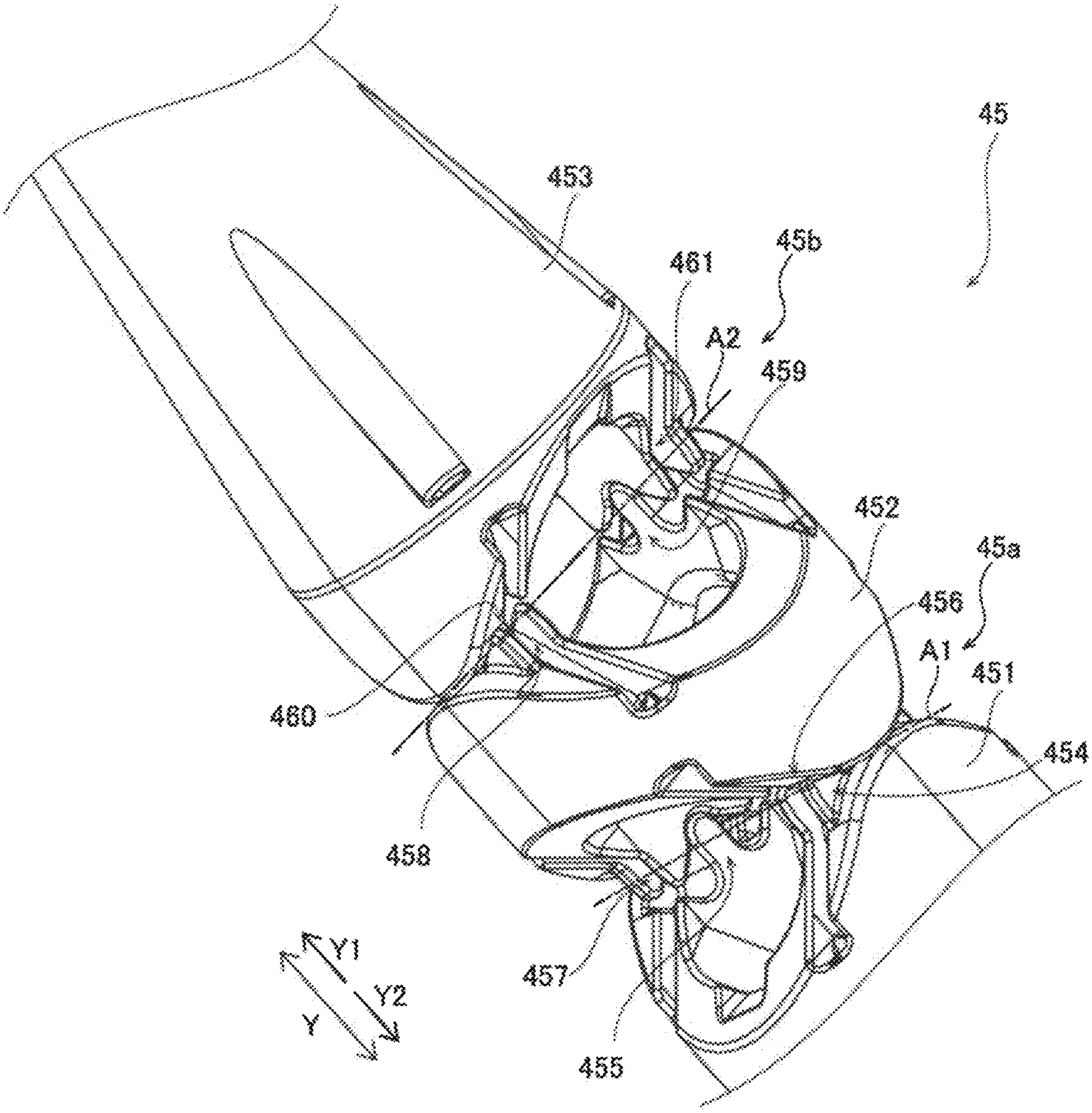
FIG. 17 is a diagram illustrating a perspective view of the wrist joint of the surgical instrument according to an embodiment.
Figure 18:
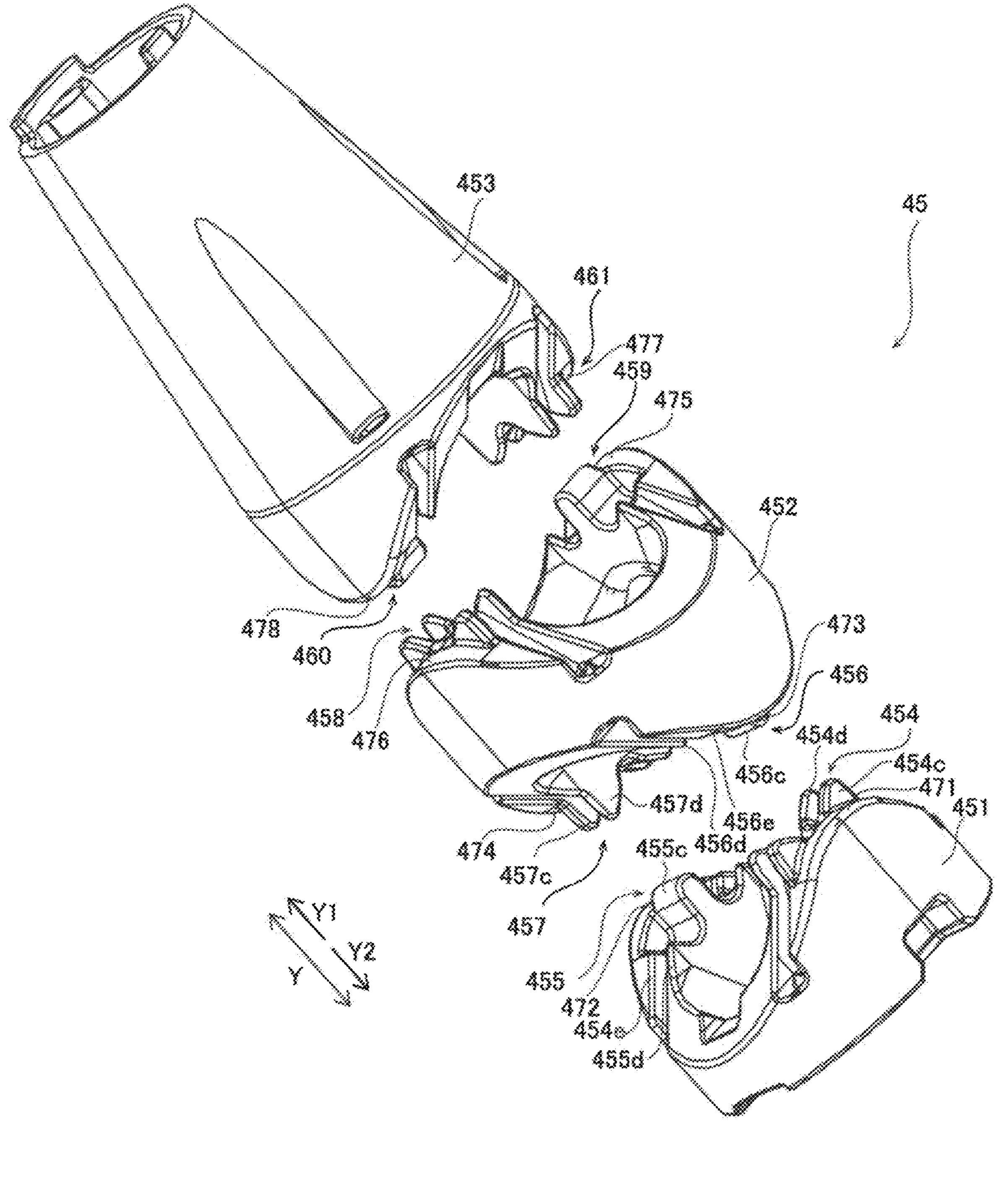
FIG. 18 is a diagram illustrating an exploded perspective view of the wrist joint of the surgical instrument according to an embodiment.

As illustrated in FIGS. 17 and 18, the wrist joint 45 includes the first joint component 451 and the second joint component 452 that is adjacent to the first joint component 451 on the distal side (Y1 side) and rotates relative to the first joint component 451. The wrist joint 45 also includes the third joint component 453 that is adjacent to the second joint component 452 on the distal side (Y1 side) and rotates relative to the second joint component 452. As illustrated in FIGS. 10 and 17, the second joint component 452 is rotatable relative to the first joint component 451 about the rotation axis A1. The rotation axis A1 extends in the direction orthogonal to the longitudinal direction (Y direction) of the shaft 42. Further, the third joint component 453 is rotatable relative to the second joint component 452 about the rotation axis A2 that is orthogonal to the rotation axis A1. The rotation axis A2 extends in the direction orthogonal to the rotation axis A1 when viewed in the longitudinal direction (Y direction) of the shaft 42.

The first joint component 451 includes a first meshing portion 454, a second meshing portion 455 arranged so as to be opposed to the first meshing portion 454 in a radial direction (A1 direction) orthogonal to the longitudinal direction of the shaft, a first contact portion 471 located radially outside of and adjacent to the first meshing portion 454, and a second contact portion 472 provided radially outside of and adjacent to the second meshing portion 455. The first meshing portion 454, the second meshing portion 455, the first contact portion 471, and the second contact portion 472 are provided at the end portion on the distal side (the Y1 side) of the first joint component 451.

The second joint component 452 includes a third meshing portion 456 that meshes with the first meshing portion 454, a fourth meshing portion 457 that is provided so as to be opposed to the third meshing portion 456 in the radial direction (A1 direction) and meshes with the second meshing portion 455, a third contact portion 473 that is in contact with the first contact portion 471, and a fourth contact portion 474 that is in contact with the second contact portion 472. The third meshing portion 456, the fourth meshing portion 457, the third contact portion 473 and the fourth contact portion 474 are provided at the end portion on the proximal side (Y2 side) of the second joint component 452. The contact between the first contact portion 471 and the third contact portion 473 reduces the load between the first meshing portion 454 and the third meshing portion 456. The contact between the second contact portion 472 and the fourth contact portion 474 reduces the load between the second meshing portion 455 and the fourth meshing portion 457.

The second joint component 452 also includes a fifth meshing portion 458, a sixth meshing portion 459 provided so as to be opposed to the fifth meshing portion 458 in the radial direction (A2 direction), a fifth contact portion 475 located radially outward of and adjacent to the fifth meshing portion 458, and a sixth contact portion 476 provided radially outside of and adjacent to the sixth meshing portion 459. The fifth meshing portion 458, the sixth meshing portion 459, the fifth contact portion 475 and the sixth contact portion 476 are provided at the end portion on the distal side (the Y1 side) of the second joint component 452.

The third joint component 453 includes a seventh meshing portion 460 that meshes with the fifth meshing portion 458, an eighth meshing portion 461 that is arranged so as to be opposed to the seventh meshing portion 460 in the radial direction (A2 direction) and meshes with the sixth meshing portion 459, a seventh contact portion 477 that is in contact with the fifth contact portion 475, and an eighth contact portion 478 that is in contact with the sixth contact portion 476. The seventh meshing portion 460, the eighth meshing portion 461, the seventh contact portion 477, and the eighth contact portion 478 are provided at the end portion on the proximal side (the Y2 side) of the third joint component 453. The contact between the fifth contact portion 475 and the seventh contact portion 477 reduces the load between the fifth meshing portion 458 and the seventh meshing portion 460. The contact between the sixth contact portion 476 and the eighth contact portion 478 reduces the load between the sixth meshing portion 459 and the eighth meshing portion 461.

As illustrated in FIG. 18, the first meshing portion 454 and the second meshing portion 455 have different shapes from each other. The third meshing portion 456 and the fourth meshing portion 457 have different shapes from each other. This makes it difficult for the first meshing portion 454 of the first joint component 451 and the fourth meshing portion 457 of the second joint component 452 to mesh with each other, and makes it difficult for the second meshing portion 455 of the first joint component 451 and the third meshing portion 456 of the second joint component 452 to mesh with each other. This allows the first and third meshing portions 454 and 456 to be properly meshed, and the second and fourth meshing portions 455 and 457 to be properly meshed, when the first and second joint components 451 and 452 are assembled together. As a result, the wrist joint can be easily and accurately assembled, and even if a problem occurs, the cause of the problem can be easily identified, allowing for appropriate quality control of the surgical instrument.

Further, the fifth meshing portion 458 and the sixth meshing portion 459 have shapes different from each other. The seventh meshing portion 460 and the eighth meshing portion 461 have shapes different from each other. This also enables accurate assembly of the wrist joint and appropriate quality control of the surgical instrument.

Further, the first meshing portion 454 and the fourth meshing portion 457 have the same shape as each other. The second meshing portion 455 and the third meshing portion 456 have the same shape as each other. This allows the meshing structure of the first meshing portion 454 and the third meshing portion 456 to be the same as the meshing structure of the second meshing portion 455 and the fourth meshing portion 457, so that the joint movement of the wrist joint 45 can be supported in a well-balanced manner by the two meshing structures between the first joint component 451 and the second joint component 452.

The fifth meshing portion 458 and the eighth meshing portion 461 have the same shape as each other. The sixth meshing portion 459 and the seventh meshing portion 460 have the same shape as each other. This also makes it possible to support the joint movement of the wrist joint 45 in a well-balanced manner with the two meshing structures between the second joint component 452 and the third joint component 453.

Moreover, the first meshing portion 454, the fourth meshing portion 457, the fifth meshing portion 458, and the eighth meshing portion 461 have the same shape as one another. The second meshing portion 455, the third meshing portion 456, the sixth meshing portion 459 and the seventh meshing portion 460 have the same shape as one another. In other words, the first meshing portion 454 and the fifth meshing portion 458 have the same configuration as each other, and the second meshing portion 455 and the sixth meshing portion 459 have the same configuration as each other. Further, the third meshing portion 456 and the seventh meshing portion 460 have the same configuration as each other, and the fourth meshing portion 457 and the eighth meshing portion 461 have the same configuration as each other. Accordingly, the description of the fifth meshing portion 458, the sixth meshing portion 459, the seventh meshing portion 460, and the eighth meshing portion 461 will be omitted as appropriate for eliminating redundancy.

Figure 19:
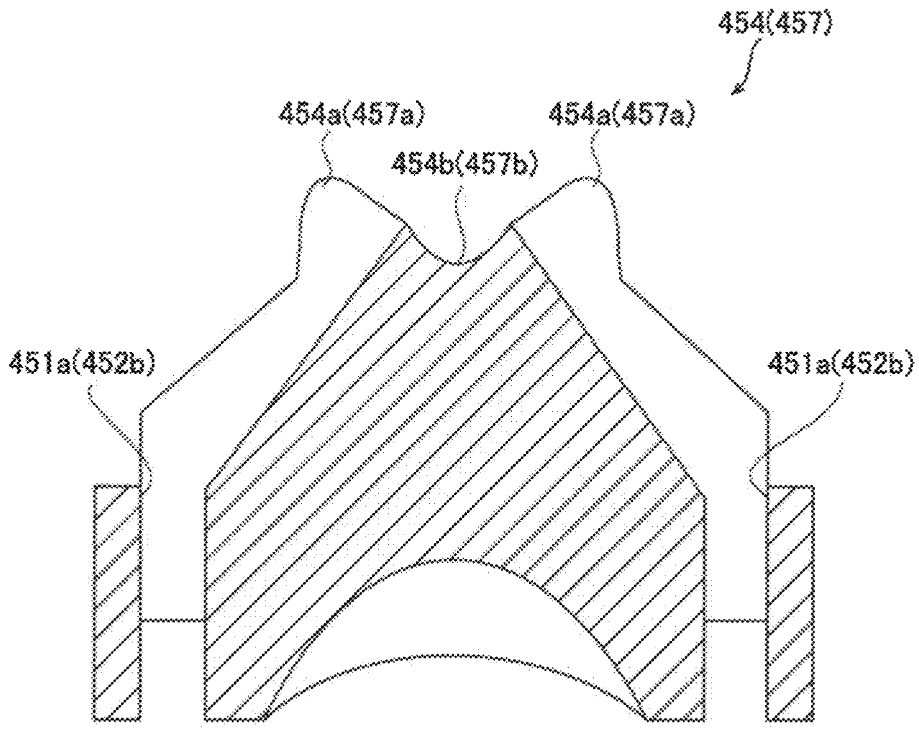
FIG. 19 is a diagram illustrating a cross-sectional view of first and fourth meshing portions of the wrist joint of the surgical instrument according to an embodiment.

As illustrated in FIG. 19, the first meshing portion 454 includes a pair of first protrusions 454*a* arranged along the rotation direction of the second joint component 452, and a first recess 454*b* arranged between the pair of first protrusions 454*a*. In the same manner, the fourth meshing portion 457 includes a pair of fourth protrusions 457*a* arranged along the rotation direction of the second joint component 452, and a fourth recess 457*b* arranged between the pair of fourth protrusions 457*a*.

Figure 20:
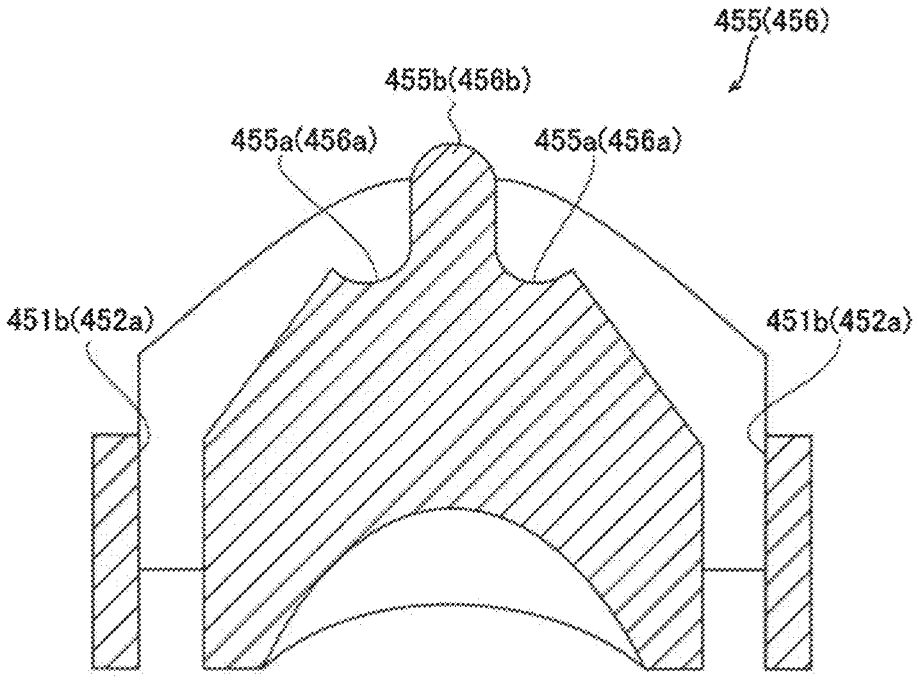
FIG. 20 is a diagram illustrating a cross-sectional view illustrating second and third meshing portions of the wrist joint of the surgical instrument according to an embodiment.

As illustrated in FIG. 20, the second meshing portion 455 includes a pair of second recesses 455*a* arranged along the rotation direction of the second joint component 452, and a second protrusion 455*b* arranged between the pair of second recesses 455*a*. In the same manner, the third meshing portion 456 includes a pair of third recesses 456*a* arranged along the rotation direction of the second joint component 452, and a third protrusion 456*b* arranged between the pair of third recesses 456*a*.

This makes it possible to prevent the first meshing portion 454 having the first recess 454*b* and the fourth meshing portion 457 having the fourth recess 457*b* from easily meshing with each other, and also makes it possible to prevent the second meshing portion 455 having the second protrusion 455*b* and the third meshing portion 456 having the third protrusion 456*b* from easily meshing with each other. As a result, it is possible to effectively prevent the first joint component 451 and the second joint component 452 from being assembled in a wrong direction.

Figure 21:
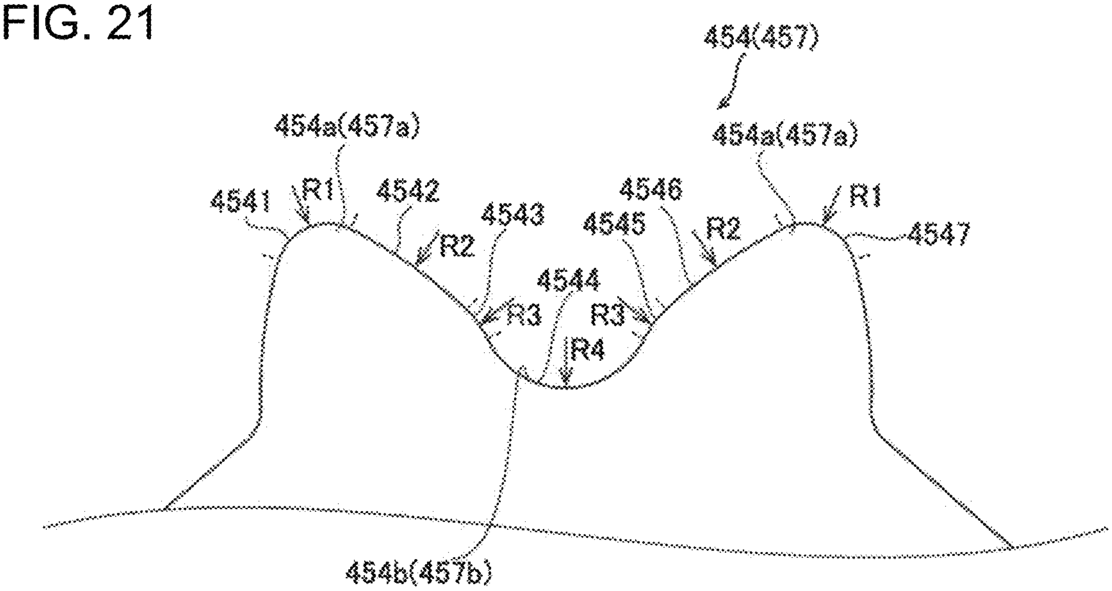
FIG. 21 is a diagram illustrating an enlarged view of the first and fourth meshing portions of the wrist joint of the surgical instrument according to an embodiment.
Figure 22:
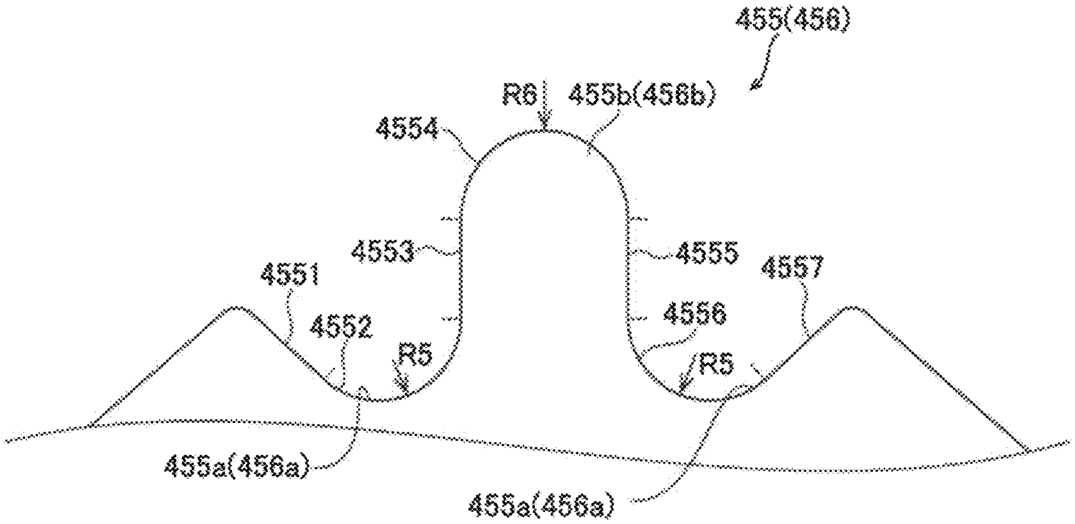
FIG. 22 is a diagram illustrating an enlarged view of the second and third meshing portions of the wrist joint of the surgical instrument according to an embodiment.

As illustrated in FIGS. 21 and 22, each of the first meshing portion 454, the second meshing portion 455, the third meshing portion 456 and the fourth meshing portion 457 have a shape in which arcs are connected together, or a shape in which arcs and straight lines are connected together, when viewed in the rotation axis direction of the second joint component 452 (A1 direction). This makes it possible to easily design the first meshing portion 454, the second meshing portion 455, the third meshing portion 456, and the fourth meshing portion 457. In addition, the shapes of the first meshing portion 454, the second meshing portion 455, the third meshing portion 456, and the fourth meshing portion 457 can be easily inspected, so that the shapes of the first meshing portion 454, the second meshing portion 455, the third meshing portion 456, and the fourth meshing portion 457 can be more appropriately managed.

Specifically, the first meshing portion 454 and the fourth meshing portion 457 each have a shape in which arcs are connected, as illustrated in FIG. 21. The first meshing portion 454 and the fourth meshing portion 457 each have an outer shape formed by connecting lines including an arc 4541 having a radius R1, an arc 4542 having a radius R2 connected to the arc 4541, an arc 4543 having a radius R3 connected to the arc 4542, an arc 4544 having a radius R4 connected to the arc 4543, an arc 4545 having the radius R3 connected to the arc 4544, an arc 4546 having the radius R2 connected to the arc 4545, and an arc 4547 having the radius R1 connected to the arc 4546. Further, the first meshing portion 454 and the fourth meshing portion 457 each have a linear symmetric shape when viewed along the rotation axis direction of the second joint component 452 (A1 direction).

As illustrated in FIG. 22, the second and third meshing portions 455 and 456 each have a shape in which arcs and straight lines are connected. The second meshing portion 455 and the third meshing portion 456 each have an outer shape formed by connecting lines including a line segment 4551, an arc 4552 having a radius R5 connected to line segment 4551, a line segment 4553 connected to the arc 4552, an arc 4554 having a radius R6 connected to the line segment 4553, a line segment 4555 connected to the arc 4554, an arc 4556 having the radius R5 connected to the line segment 4555, and a line segment 4557 connected to the arc 4556. Further, the second meshing portion 455 and the third meshing portion 456 each have a linear symmetric shape when viewed in the rotation axis direction (A1 direction) of the second joint component 452.

As illustrated in FIGS. 23 to 26, the wrist joint 45 is articulated by driving the wires 46 to rotate the second joint component 452 relative to the first joint component 451. As illustrated in FIG. 10, the wire 46 has the end portion 46*e* thereof fixed to the third joint component 453 on the end effector side (Y1 side) of the wrist joint 45.

As illustrated in FIG. 18, the first meshing portion 454 includes a first portion 454*c* and a second portion 454*d* that are separated in the radial direction (A1 direction) by a distance that allows the wires 46 to pass therethrough. Further, each of the first portion 454*c* and the second portion 454*d* is formed with the first protrusions 454*a* and the first recess 454*b*. In the same manner as the first meshing portion 454, the fourth meshing portion 457 includes a third portion 457*c* and a fourth portion 457*d* that are separated in the radial direction (A1 direction) by a distance that allows the wires 46 to pass through. Further, each of the third portion 457*c* and the fourth portion 457*d* is formed with the fourth protrusions 457*a* and the fourth recess 457*b*. This prevents the wires 46 from interfering with the first portion 454*c* and the second portion 454*d* when the joint movement performed in which the second joint component 452 is rotated significantly relative to the first joint component 451 such as being illustrated in FIG. 26.

As illustrated in FIG. 18, the second meshing portion 455 includes a fifth portion 455*c* that is continuously formed in the radial direction (A1 direction). The second meshing portion 455 also includes a portion 455*d* and a portion 455*e* that are separated in the radial direction (A1 direction) by a distance that allows the wires 46 to pass therethrough. Further, the second protrusion 455*b* is formed in the fifth portion 455*c*. Further, the second recesses 455*a* are formed in each of the portion 455*d* and the portion 454*e*.

As in the second meshing portion 455, the third meshing portion 456 includes a sixth portion 456*c* that is formed continuously in the radial direction (A1 direction). The third meshing portion 456 also includes a portion 456*d* and a portion 456*e* that are separated in the radial direction (A1 direction) by a distance that allows the wires 46 to pass therethrough. Further, the third protrusion 456*b* is formed in the sixth portion 456*c*. Further, the third recesses 456*a* are formed in each of the portion 456*d* and the portion 456*e*.

As illustrated in FIG. 19, the first joint component 451 includes first through holes 451*a* which are disposed at positions spaced apart from the first meshing portion 454 and through which the wires 46 pass. As illustrated in FIG. 20, the first joint component 451 includes second through holes 451*b* which are disposed at positions spaced apart from the second meshing portion 455 and through which the wires 46 passes. As illustrated in FIG. 20, the second joint component 452 includes third through holes 452*a* which are disposed at positions spaced apart from the third meshing portion 456 and through which the wires 46 pass. As illustrated in FIG. 19, the second joint component 452 includes fourth through holes 452*b* which are disposed at positions spaced apart from the fourth meshing portion 457 and through which the wires 46 pass. This allows the through holes through which the wires 46 pass to be located at the positions away from the meshing portions, thereby preventing the meshing portions from interfering with the wires 46.

Next, with reference to FIGS. 23 to 26, the rotation of the second joint component 452 relative to the first joint component 451 is described. Although FIGS. 23 to 26 illustrate the relationship between the first meshing portion 454 of the first joint component 451 and the third meshing portion 456 of the second joint component 452, the relationship between the second meshing portion 455 of the first joint component 451 and the fourth meshing portion 457 of the second joint component 452 is in a same manner with the protrusions and the recesses interchanged, and thus illustration and description thereof is omitted for eliminating redundancy. Also the rotation of the third joint component 453 relative to the second joint component 452 takes the same or similar operation, and thus illustration and description thereof is omitted for eliminate redundancy.

Figure 23:
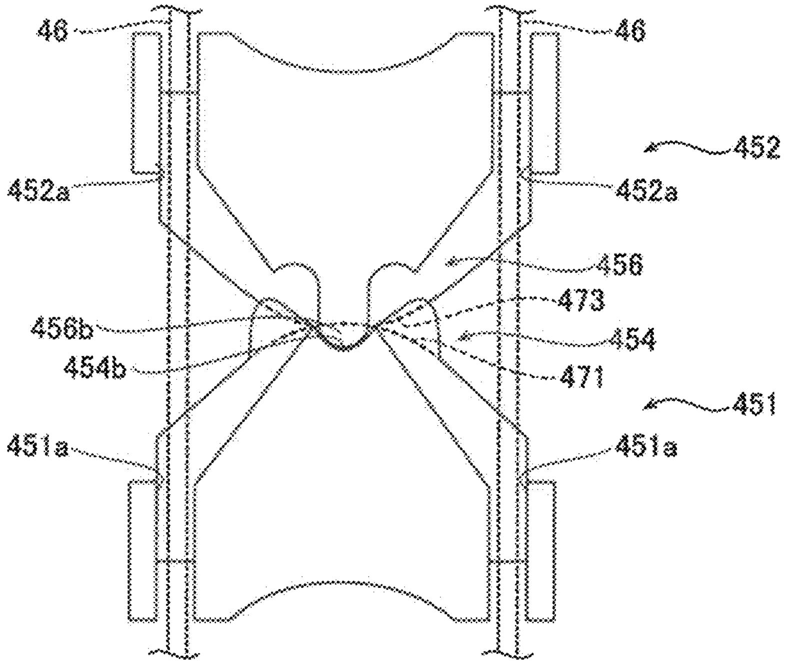
FIG. 23 is a diagram illustrating a view of the wrist joint of the surgical instrument in an unrotated state according to an embodiment.

As illustrated in FIG. 23, when the second joint component 452 is not rotated relative to the first joint component 451, the third protrusion 456*b* of the third meshing portion 456 of the second joint component 452 is fit in the first recess 454*b* of the first meshing portion 454 of the first joint component 451.

Figure 24:
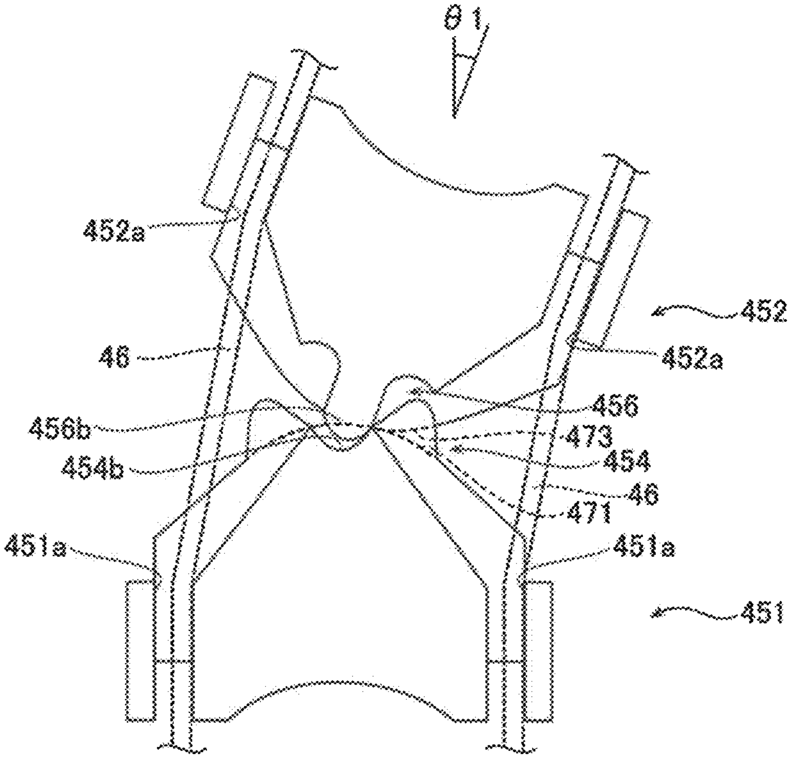
FIG. 24 is a diagram illustrating a view of the wrist joint of the surgical instrument in a state where the wrist joint is rotated by an angle θ1 according to an embodiment.

As illustrated in FIG. 24, by the operation of the wires 46, the third protrusion 456*b* of the third meshing portion 456 of the second joint component 452 is rotated with respect to the first recess 454*b* of the first meshing portion 454 of the first joint component 451 while contacting with the first recess 454*b*, so that the second joint component 452 is rotated by an angle θ1 relative to the first joint component 451.

Figure 25:
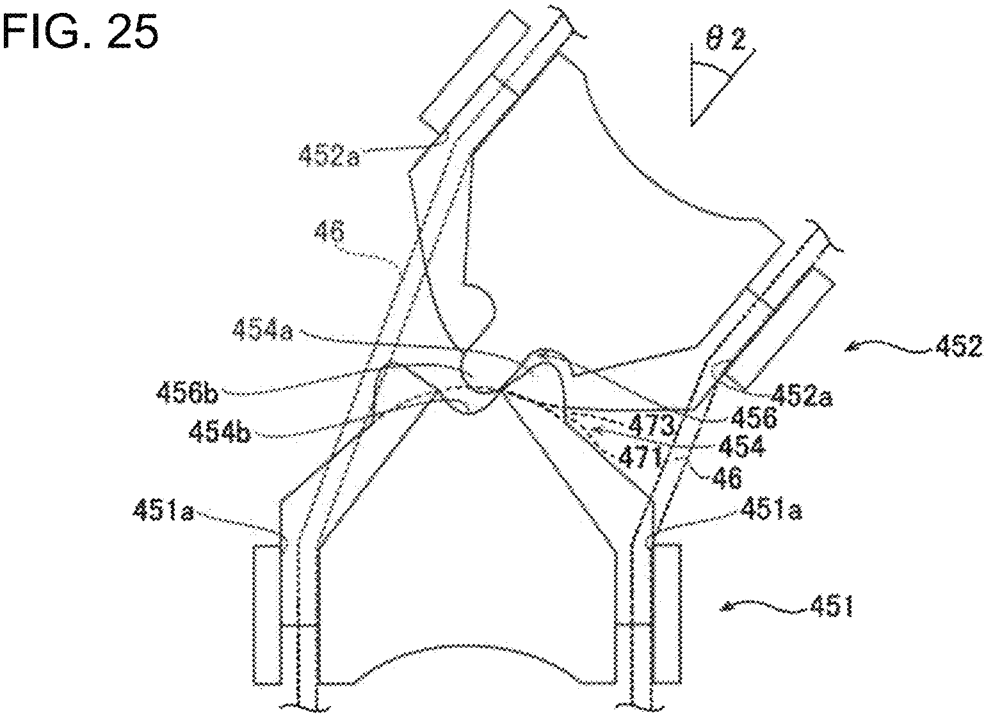
FIG. 25 is a diagram illustrating a view of the wrist joint of the surgical instrument in a state where the wrist joint is rotated by an angle θ2 according to an embodiment.

As illustrated in FIG. 25, by the operation of the wires 46, the third protrusion 456*b* of the third meshing portion 456 of the second joint component 452 is rotated with respect to the first protrusion 454*a* of the first meshing portion 454 of the first joint component 451 while contacting with the first protrusion 454*a*, so that the second joint component 452 is rotated by an angle θ2 relative to the first joint component 451. The angle θ2 is greater than the angle θ1.

Figure 26:
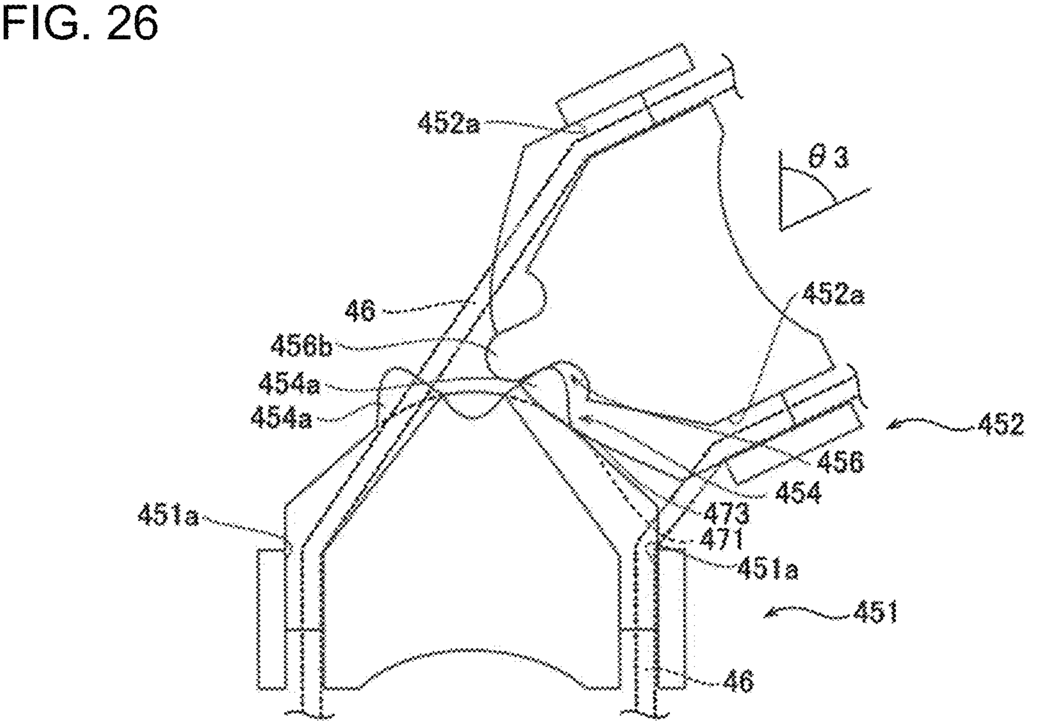
FIG. 26 is a diagram illustrating a view of the wrist joint of the surgical instrument in a state where the wrist joint is rotated by an angle θ3 according to an embodiment.

As illustrated in FIG. 26, by the operation of the wires 46, the third protrusion 456*b* of the third meshing portion 456 of the second joint component 452 is further rotated with respect to the first protrusion 454*a* of the first meshing portion 454 of the first joint component 451 while contacting with the first protrusion 454*a*, so that the second joint component 452 is rotated by an angle θ3 relative to the first joint component 451. The angle θ3 is greater than the angle θ2.

(Modifications)

Note that one or more embodiments disclosed herein should be considered as exemplary in all respects and do not limit the invention. The scope of the invention is indicated by claims, not by explanation of one or more embodiments described above, and includes equivalents to the claims and all alterations (modification) within the same.

For example, in one or more embodiments described above, a case has been described in which the four drive shafts are provided, but the invention is not limited thereto. For example, five or more drive shafts may be provided.

Further, in one or more embodiments described above, a case has been described in which the rod is provided as the elongate element, but the invention is not limited thereto. For example, the elongate element may be a wire or a cable.

Further, in one or more embodiments described above, a case has been described in which the driving force transmission part is provided between the fourth drive shaft and the lever, but the invention is not limited thereto. For example, the lever may be directly connected to the fourth drive shaft.

Further, in one or more embodiments described above, a case has been described in which the driving force transmission part includes the gear train, but the invention is not limited thereto. For example, the driving force transmission part may include a belt pulley or the like other than the gear train.

Further, in one or more embodiments described above, a case has been described in which the gear train includes the spur gear and the sector gear, but the invention is not limited thereto. For example, the gear train may include only a spur gear or only a sector gear. Also, the gear train may include a gear(s) other than the spur gear and the sector gear.

Further, in one or more embodiments described above, a case has been described in which the spring member is provided, but the invention is not limited thereto. For example, the spring member may not be provided.

The invention claimed is:

1. A surgical instrument comprising:

a housing including a base that is to be attached to a robot arm, a shaft including a proximal end connected to the base;

a wrist joint connected to a distal end side of the shaft, the wrist joint including a first joint configured to perform a pitch joint movement about a first rotation axis intersecting a longitudinal direction of the shaft and a second joint configured to perform a yaw joint movement about a second rotation axis intersecting the longitudinal direction and the first rotation axis;

an end effector connected to a distal end of the wrist joint;

an elongate element extending in the longitudinal direction of the shaft, the elongate element including a distal end thereof connected to the end effector;

at least four drive shafts provided to the base and configured to be driven to rotate by driving forces from motors provided to the robot arm;

a lever configured to move the elongate element in the longitudinal direction; and a holding member that holds the elongate element, wherein the at least four drive shafts comprise a first drive shaft configured to roll the shaft about an axis along the longitudinal direction of the shaft, a second drive shaft and a third drive shaft configured to pitch the first joint and yaw the second joint, and a fourth drive shaft configured to move the elongate element in the longitudinal direction of the shaft, the lever includes a first arm, a second arm opposed to the first arm, a connection portion connecting a first side of the first arm and a first side of the second arm, a first engagement portion provided to a second side of the first arm opposite the first side of the first arm and engaged with the holding member, a second engagement portion provided to a second side of the second arm opposite the first side of the second arm and engaged with the holding member, and a shaft portion that is provided to the first side of the first arm and is rotatably arranged on the base so as to move the first and second engagement portions by a driving force from the fourth drive shaft, and the holding member is arranged between the first engagement portion and the second engagement portion such that the holding member engages with the first engagement portion and the second engagement portion.

2. The surgical instrument according to claim 1, further comprising a driving force transmission part provided between the fourth drive shaft and the lever and configured to transmit the driving force from the fourth drive shaft to the lever.

3. The surgical instrument according to claim 2, wherein the driving force transmission part includes a gear train including a first gear and a second gear, and is configured to transmit the driving force from the fourth drive shaft to the lever through the gear train.

4. The surgical instrument according to claim 2, wherein the driving force transmission part is configured to transmit rotation of the fourth drive shaft to the lever with decelerating a speed of the rotation of the fourth drive shaft.

5. The surgical instrument according to claim 1, wherein the end effector includes a first jaw and a second jaw, and the first jaw includes a support shaft rotatably supported by the second jaw and a connection portion connected to the distal end of the elongate element, and is configured to rotate about an axis of the support shaft due to the movement of the elongate element in the longitudinal direction.

6. The surgical instrument according to claim 1, further comprising a spring member that biases the holding member toward the distal end side of the shaft in the longitudinal direction, wherein the first and second engagement portions are engaged with the elongate element via the holding member.

7. The surgical instrument according to claim 1, wherein the elongate element is a rod that includes a bendable wire at a portion corresponding to the wrist joint.

8. The surgical instrument according to claim 1, further comprising first to fourth wires extending in the longitudinal direction of the shaft, wherein the wrist joint includes a first joint component connected to the distal end side of the shaft, a second joint component connected to the first joint component via the first joint, and a third joint component connected to the second joint component via the second joint, and the first to fourth wires includes distal ends thereof fixed to the third joint component.

9. The surgical instrument according to claim 8, wherein a cross section of the third joint component includes four regions defined by a first plane parallel to both the longitudinal direction of the shaft and the first rotation axis and a second plane parallel to both the longitudinal direction of the shaft and the second rotation axis, the first to fourth wires pass through the four regions, respectively, and proximal ends of the first wire and the second wire are wound around and fixed to the second drive shaft, and proximal ends of the third wire and the fourth wire are wound around and fixed to the third drive shaft.

10. The surgical instrument according to claim 8, wherein the second drive shaft is configured to rotate in a first direction to apply tension to the first wire and to rotate in a second direction opposite the first direction to apply tension to the second wire, the third drive shaft is configured to rotate in a third direction to apply tension to the third wire and to rotate in a fourth direction opposite to the third direction to apply tension to the fourth wire, the first joint is configured, when the rotation of the second drive shaft applies the tension to the first wire and the rotation of the third drive shaft applies the tension to the fourth wire, or when the rotation of the second drive shaft applies the tension to the second wire and the rotation of the third drive shaft applies the tension to the third wire, to perform the pitch joint movement about the first rotation axis, and the second joint is configured, when the rotation of the second drive shaft applies the tension to the first wire and the rotation of the third drive shaft applies the tension to the third wire, or when the rotation of the second drive shaft applies the tension to the second wire and the rotation of the third drive shaft applies the tension to the fourth wire, to perform the yaw joint movement around the second rotation axis.

11. The surgical instrument according to claim 1, wherein the housing includes a frame member, and the lever includes a second shaft portion that is provided to the first side of the second arm and is rotatably arranged on the frame member.

12. A surgical instrument comprising:

a housing including a base that is to be attached to a robot arm;

a shaft including a proximal end connected to the base;

a wrist joint connected to a distal end side of the shaft, the wrist joint including a first joint configured to perform a pitch joint movement about a first rotation axis intersecting a longitudinal direction of the shaft and a second joint configured to perform a yaw joint movement about a second rotation axis intersecting the longitudinal direction and the first rotation axis; and an end effector connected to a distal end of the wrist joint, wherein the wrist joint includes a first joint component connected to the distal end side of the shaft, and a second joint component connected to the first joint component via the first joint, the first joint component includes a first meshing portion and a second meshing portion provided to be opposed to the first meshing portion in a radial direction orthogonal to the longitudinal direction of the shaft, the second joint component includes a third meshing portion that meshes with the first meshing portion, and a fourth meshing portion that is provided to be opposed to the third meshing portion in the radial direction and meshes with the second meshing portion, the first and second meshing portions have different shapes from each other, the third meshing portion and the fourth meshing portion have different shapes from each other, the first meshing portion and the fourth meshing portion have a same shape as each other, and the second meshing portion and the third meshing portion have a same shape as each other.

13. The surgical instrument according to claim 12, wherein the first meshing portion includes a pair of first protrusions arranged along a rotation direction of the second joint component, and a first recess arranged between the pair of first protrusions, the second meshing portion includes a pair of second recesses arranged along the rotation direction of the second joint component and a second protrusion arranged between the pair of second recesses, the third meshing portion includes a pair of third recesses arranged along the rotation direction of the second joint component and a third protrusion arranged between the pair of third recesses, and the fourth meshing portion includes a pair of fourth protrusions arranged along the rotation direction of the second joint component, and a fourth recess arranged between the pair of fourth protrusions.

14. The surgical instrument according to claim 12, wherein the first meshing portion, the second meshing portion, the third meshing portion, and the fourth meshing portion each have a shape in which arcs are connected together, or a shape in which arcs and straight lines are connected together, in a view along a direction of a rotation axis of the second joint component.

15. The surgical instrument according to claim 12, wherein the wrist joint includes a third joint component connected to the second joint component via the second joint, the second joint component includes a fifth meshing portion and a sixth meshing portion provided to be opposed to the fifth meshing portion in the radial direction, the third joint component includes a seventh meshing portion meshing with the fifth meshing portion, and an eighth meshing portion provided to be opposed to the seventh meshing portion in the radial direction and meshing with the sixth meshing portion, the fifth meshing portion and the sixth meshing portion have different shapes from each other, the seventh meshing portion and the eighth meshing portion have different shapes from each other, the fifth meshing portion and the eighth meshing portion have a same shape as each other, and the sixth meshing portion and the seventh meshing portion have a same shape as each other.

16. The surgical instrument according to claim 12, wherein the first joint component includes a first contact portion adjacent to the first meshing portion and a second contact portion adjacent to the second meshing portion.

17. A surgical instrument comprising:

a housing including a base that is to be attached to a robot arm, a shaft including a proximal end connected to the base;

a wrist joint connected to a distal end side of the shaft, the wrist joint including a first joint configured to perform a pitch joint movement about a first rotation axis intersecting a longitudinal direction of the shaft and a second joint configured to perform a yaw joint movement about a second rotation axis intersecting the longitudinal direction and the first rotation axis;

an end effector connected to a distal end of the wrist joint; and at least four drive shafts provided to the base and configured to be driven to rotate by driving forces from motors provided to the robot arm, wherein the at least four drive shafts comprise a first drive shaft configured to roll the shaft about an axis along the longitudinal direction of the shaft, a second drive shaft and a third drive shaft configured to pitch the first joint and yaw the second joint, and a fourth drive shaft configured to drive the end effector, the wrist joint includes a first joint component and a second joint component that is adjacent to the first joint component and provided on a distal side of the first joint component and is rotatable relative to the first joint component, the first joint component includes a first meshing portion and a second meshing portion provided to be opposed to the first meshing portion in a radial direction orthogonal to the longitudinal direction of the shaft, the second joint component includes a third meshing portion that meshes with the first meshing portion, and a fourth meshing portion that is provided to be opposed to the third meshing portion in the radial direction and meshes with the second meshing portion, the first meshing portion and the second meshing portion have different shapes from each other, and the third meshing portion and the fourth meshing portion have different shapes from each other.

18. The surgical instrument according to claim 17, wherein the first meshing portion and the fourth meshing portion have a same shape as each other, and the second meshing portion and the third meshing portion have a same shape as each other.

19. The surgical instrument according to claim 17, wherein the first joint component includes a first contact portion adjacent to the first meshing portion and a second contact portion adjacent to the second meshing portion, the second joint component includes a third contact portion adjacent to the third meshing portion and contacting to the first contact portion and a fourth contact portion adjacent to the fourth meshing portion and contacting to the second contact portion.

20. The surgical instrument according to claim 17, wherein the wrist joint includes a third joint component connected to the second joint component via the second joint, the second joint component includes a fifth meshing portion and a sixth meshing portion provided to be opposed to the fifth meshing portion in the radial direction, the third joint component includes a seventh meshing portion meshing with the fifth meshing portion, and an eighth meshing portion provided to be opposed to the seventh meshing portion in the radial direction and meshing with the sixth meshing portion, the fifth meshing portion and the sixth meshing portion have different shapes from each other, and the seventh meshing portion and the eighth meshing portion have different shapes from each other.

* * * * *